US012062177B2

(12) United States Patent
Atria et al.

(10) Patent No.: US 12,062,177 B2
(45) Date of Patent: Aug. 13, 2024

(54) SYSTEMS AND METHODS FOR X-RAY TOMOSYNTHESIS IMAGE RECONSTRUCTION

(71) Applicant: nView medical Inc., Salt Lake City, UT (US)

(72) Inventors: Cristian Atria, Salt Lake City, UT (US); Arvidas B. Cheryauka, Salt Lake City, UT (US); Lisa M. Last, Salt Lake City, UT (US)

(73) Assignee: nView medical Inc., Salt Lake City, UT (US)

( * ) Notice: Subject to any disclaimer, the term of this patent is extended or adjusted under 35 U.S.C. 154(b) by 843 days.

(21) Appl. No.: 17/100,097

(22) Filed: Nov. 20, 2020

(65) Prior Publication Data

US 2021/0073999 A1 Mar. 11, 2021

Related U.S. Application Data

(63) Continuation of application No. 15/469,301, filed on Mar. 24, 2017, now Pat. No. 10,846,860, which is a (Continued)

(51) Int. Cl.
| | | |
|---|---|---|
| *G06T 7/11* | (2017.01) | |
| *A61B 6/03* | (2006.01) | |
| *G06T 11/00* | (2006.01) | |

(52) U.S. Cl.
CPC ............. *G06T 7/11* (2017.01); *A61B 6/032* (2013.01); *G06T 11/006* (2013.01); *G06T 2200/04* (2013.01)

(58) Field of Classification Search
CPC ..... G06T 7/11; G06T 11/006; G06T 2200/04; A61B 6/032
(Continued)

(56) References Cited

U.S. PATENT DOCUMENTS

| 5,442,674 A | 8/1995 | Picard et al. |
| 5,734,483 A | 3/1998 | Itoh |
(Continued)

FOREIGN PATENT DOCUMENTS

| DE | 102007037966 A1 | 2/2009 |
| DE | 102009043421 A1 | 4/2011 |
(Continued)

OTHER PUBLICATIONS

Wu et al.; "Iterative Low-Dose CT Reconstruction with Priors Trained by Artificial Neural Network." IEEE Transaction On Medical Imaging, vol. 36, No. 12; Sep. 15, 2017; pp. 2479-2486.
(Continued)

*Primary Examiner* — Jason L McCormack
(74) *Attorney, Agent, or Firm* — Thorpe North & Western, LLP

(57) ABSTRACT

Imaging systems comprising x-ray image reconstruction systems combined with optical imaging and/or tracking systems. In some embodiments, the imaging system may comprise an x-ray image reconstruction system configured to generate three-dimensional image data of at least an internal portion of a target object under a surface of the target object and a three-dimensional optical imaging system configured to reconstruct an image of at least a portion of the surface of the target object by generating surface three-dimensional image data. The three-dimensional optical imaging system may be registered to the x-ray tomosynthesis image reconstruction system such that three-dimensional image data from the x-ray tomosynthesis image reconstruction system and three-dimensional image data from the three-dimensional optical imaging system may be used as a constraint to improve image quality of an image of the target object.

12 Claims, 26 Drawing Sheets

Related U.S. Application Data continuation-in-part of application No. 14/198,390, filed on Mar. 5, 2014, now Pat. No. 10,070,828.

(60) Provisional application No. 62/313,041, filed on Mar. 24, 2016, provisional application No. 61/773,025, filed on Mar. 5, 2013.

(58) Field of Classification Search
USPC ........................................................ 382/132
See application file for complete search history.

(56) References Cited

U.S. PATENT DOCUMENTS

| | | | |
|---|---|---|---|
| 6,081,580 A | 6/2000 | Grodzins et al. |
| 6,120,180 A | 9/2000 | Graumann |
| 6,139,183 A | 10/2000 | Graumann |
| 6,206,566 B1 | 3/2001 | Schuetz |
| 6,222,902 B1 | 4/2001 | Lin et al. |
| 6,256,370 B1 | 7/2001 | Yavuz |
| 6,292,530 B1 | 9/2001 | Yavus et al. |
| 6,400,789 B1 | 6/2002 | Dafnl |
| 6,442,288 B1 | 8/2002 | Haerer et al. |
| 6,483,890 B1 | 11/2002 | Malamud |
| 6,491,430 B1 | 12/2002 | Seissler |
| 6,582,120 B2 | 6/2003 | Schomberg |
| 6,654,149 B1 | 11/2003 | Sheng |
| 6,731,283 B1 | 5/2004 | Navab |
| 6,782,287 B2 | 8/2004 | Grzeszczuk et al. |
| 6,814,489 B2 | 11/2004 | Jensen et al. |
| 6,940,943 B2 | 9/2005 | Claus et al. |
| 7,167,538 B2 | 1/2007 | Strobel et al. |
| 7,245,698 B2 | 7/2007 | Pang et al. |
| 7,356,113 B2 | 4/2008 | Wu et al. |
| 7,369,695 B2 | 5/2008 | Zettel et al. |
| 7,433,507 B2 | 10/2008 | Jabri et al. |
| 7,478,949 B2 | 1/2009 | Niessen et al. |
| 7,494,278 B2 | 2/2009 | Ritter |
| 7,558,366 B2 | 7/2009 | Barth et al. |
| 7,620,223 B2 | 11/2009 | Xu et al. |
| 7,628,538 B2 | 12/2009 | Dehler |
| 7,630,753 B2 | 12/2009 | Simon et al. |
| 7,684,542 B2 | 3/2010 | Blohm et al. |
| 7,712,961 B2 | 5/2010 | Horndler et al. |
| 7,742,557 B2 | 6/2010 | Brunner et al. |
| 7,756,567 B2 | 7/2010 | Kuduvalli et al. |
| 7,766,548 B2 | 8/2010 | Dehler et al. |
| 7,806,588 B2 | 10/2010 | Brunner et al. |
| 7,835,784 B2 | 11/2010 | Mire et al. |
| 7,869,561 B2 | 1/2011 | Dafni |
| 7,936,858 B2 | 5/2011 | Hashemi et al. |
| 7,996,064 B2 | 8/2011 | Simon et al. |
| 8,041,094 B2 | 10/2011 | Bernard et al. |
| 8,094,773 B2 | 1/2012 | Boese et al. |
| 8,189,735 B2 | 5/2012 | Khare et al. |
| 8,254,518 B2 | 8/2012 | Paidi et al. |
| 8,320,612 B2 | 11/2012 | Knobel et al. |
| 8,472,685 B2 | 6/2013 | Chien et al. |
| 8,594,407 B2 | 11/2013 | Jerebko et al. |
| 8,767,909 B2 | 7/2014 | Vogtmeier |
| 8,774,355 B2 | 7/2014 | Claus et al. |
| 9,020,230 B2 | 4/2015 | Yu et al. |
| 2005/0078861 A1 | 4/2005 | Usikov |
| 2005/0123089 A1 | 6/2005 | Man |
| 2005/0135664 A1 | 6/2005 | Kaufhold et al. |
| 2006/0097131 A1 | 5/2006 | Ohara |
| 2006/0098855 A1 | 5/2006 | Gkanatsios et al. |
| 2006/0142984 A1 | 6/2006 | Weese et al. |
| 2006/0251313 A1 | 11/2006 | Lievin et al. |
| 2007/0025509 A1 | 2/2007 | Pang et al. |
| 2007/0040854 A1 | 2/2007 | Lievin et al. |
| 2007/0100234 A1 | 5/2007 | Arenson et al. |
| 2008/0009717 A1 | 1/2008 | Herrmann et al. |
| 2008/0095300 A1 | 4/2008 | Zingelewicz et al. |
| 2009/0068620 A1 | 3/2009 | Knobel et al. |
| 2009/0086889 A1 | 4/2009 | Hashemi et al. |
| 2009/0088773 A1* | 4/2009 | Zhao .................. A61B 34/37 606/130 |
| 2009/0092225 A1 | 4/2009 | Boese et al. |
| 2009/0136902 A1 | 5/2009 | Zundorf et al. |
| 2009/0191509 A1 | 7/2009 | Zudorf et al. |
| 2009/0198124 A1 | 8/2009 | Adamus et al. |
| 2009/0202046 A1 | 8/2009 | Brunner et al. |
| 2009/0297011 A1 | 12/2009 | Brunner et al. |
| 2010/0067231 A1 | 3/2010 | Simon et al. |
| 2010/0124311 A1 | 5/2010 | Enomoto et al. |
| 2010/0246778 A1 | 9/2010 | Heigl et al. |
| 2010/0284601 A1 | 11/2010 | Rubner et al. |
| 2010/0292565 A1 | 11/2010 | Meyer et al. |
| 2011/0058647 A1 | 3/2011 | Star-Lack et al. |
| 2011/0064286 A1 | 3/2011 | Chien et al. |
| 2011/0075794 A1 | 3/2011 | Boese et al. |
| 2011/0080996 A1 | 4/2011 | Paidi et al. |
| 2011/0135173 A1 | 6/2011 | Elbaroudi et al. |
| 2011/0210261 A1 | 9/2011 | Mauer, Jr. |
| 2011/0282181 A1 | 11/2011 | Wang et al. |
| 2012/0008734 A1 | 1/2012 | Thomson et al. |
| 2012/0087466 A1 | 4/2012 | Klingenbeck |
| 2012/0243655 A1 | 9/2012 | Ninomiya et al. |
| 2012/0302880 A1 | 11/2012 | Tian et al. |
| 2013/0294570 A1 | 11/2013 | Hansis |
| 2014/0140601 A1 | 5/2014 | Livitin et al. |
| 2015/0125059 A1 | 5/2015 | Holmes et al. |
| 2015/0201890 A1 | 7/2015 | Maidment et al. |
| 2016/0163073 A1 | 6/2016 | Grass et al. |
| 2017/0076198 A1 | 3/2017 | Jin et al. |
| 2017/0178365 A1 | 6/2017 | Raupach et al. |
| 2018/0374245 A1 | 12/2018 | Xu et al. |
| 2019/0108441 A1 | 4/2019 | Thibault et al. |
| 2019/0325618 A1 | 10/2019 | Yang et al. |
| 2020/0085392 A1 | 3/2020 | Lanza et al. |
| 2021/0150779 A1 | 5/2021 | Anastasio et al. |

FOREIGN PATENT DOCUMENTS

| | | | |
|---|---|---|---|
| EP | 3150124 A1 | 4/2017 | |
| JP | 2010057731 A | 3/2010 | |
| JP | 2014-518133 A | 7/2014 | |
| WO | WO 2007/115825 A1 | 10/2007 | |
| WO | WO-2011134083 A1 * | 11/2011 | ............. A61B 34/20 |
| WO | WO 2011134676 A2 | 11/2011 | |

OTHER PUBLICATIONS

Farsiu et al.; "Fast and Robust Multiframe Super Resolution;" IEEE Transactions on Image Processing; (Oct. 2004); pp. 1327-1344; vol. 13, No. 10; <doi: 10.1109/TIP.2004.834669 >.

Sunnegardh; "Iterative Filtered Backprojection Methods for Helical Cone-Beam CT;" [Dissertation]; Linköping Studies in Science and Technology; (Aug. 2009); 180 pages; No. 1264.

Zhu et al.; "Unpaired Image-to-Image Translation using Cycle-Consistent Adversarial Networks;" IPSJ SIG Technical Report; (2017); 19 pages; vol. 2017-CG-167, No. 5; English Translation included.

Davidhazy; "Slip Scan and Strip Photography Overview"; Imaging and Photographic Technology, School of Photo Arts and Sciences, Rochester Institute of Technology; http://web.archive.org/web/20100704083756/http://people.rit.edu/andpph/text-streak-strip-scanning-imaging-overview.html (accessed from archive.org Jul. 4, 2010); 6 pages.

Galigekere et al.; "Cone-beam Reprojection Using Projection Matrices"; IEEE Transactions on Medical Imaging; (2003); pp. 1202-1214; vol. 22, Issue 10; IEEE.

Gordon et al.; "Algebraic Reconstruction Techniques (ART) for Three-dimensional Electron Microscopy and X-ray Photography"; Journal of Theoretical Biology; (1970); pp. 471-481; vol. 29.

Joshi et al.; "DigiWarp: a method for deformable mouse atlas warping to surface topographic data." Phys Med Biol. Oct. 21, 2010: 55(10): 6197-6214 (Year: 2010).

Lyra et al.; "Filtering in SPECT Image Reconstruction." International Journal of Biomedical Imaging vol. 2011, Article ID 693795 (Year: 2011).

(56) References Cited

OTHER PUBLICATIONS

Schlemper et al.; "A Deep Cascade of Convolutional Neural Networks for MR Image Reconstruction;" In: Cornell University Library; (Mar. 1, 2017); 12 pages; [online] [retrieved on Dec. 27, 2018]; Retrieved from <URL: https://arxiv.org/abs/1703.00555 >.

Sidky et al.; "Accurate image reconstruction from few-views and limited-angle data in divergent-beam CT"; Journal of X-Ray Science and Technology; (2006); pp. 119-139; vol. 14; IOS Press.

Schlemper et al.; "A Deep Cascade of Convolutional Neural Networks for MR Image Reconstruction"; IEEE Transactions on Medical Imaging; (Feb. 2018); pp. 491-503; vol. 37, No. 2; <doi: 10.1109/TMI.2017.2760978 >.

\* cited by examiner

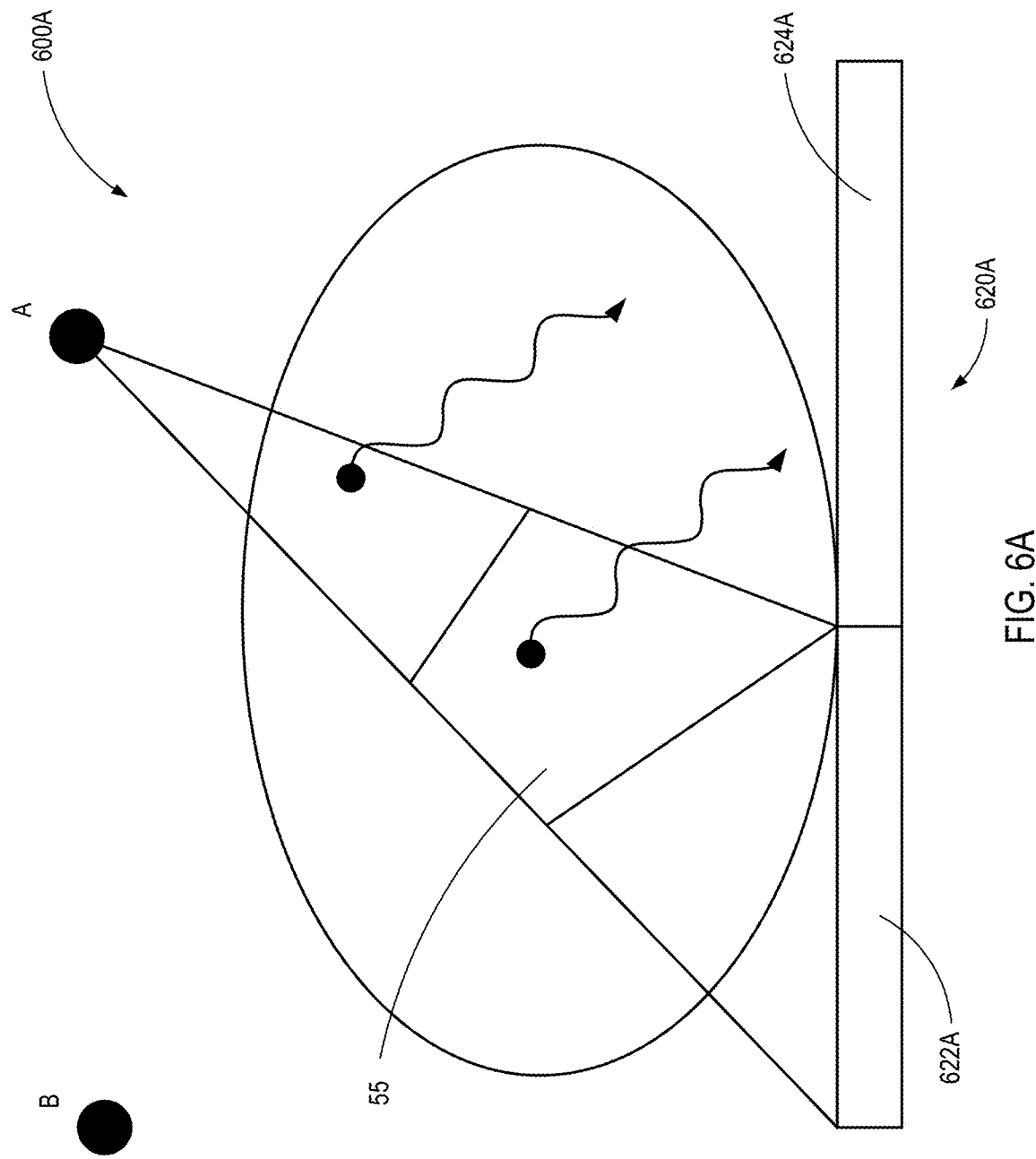

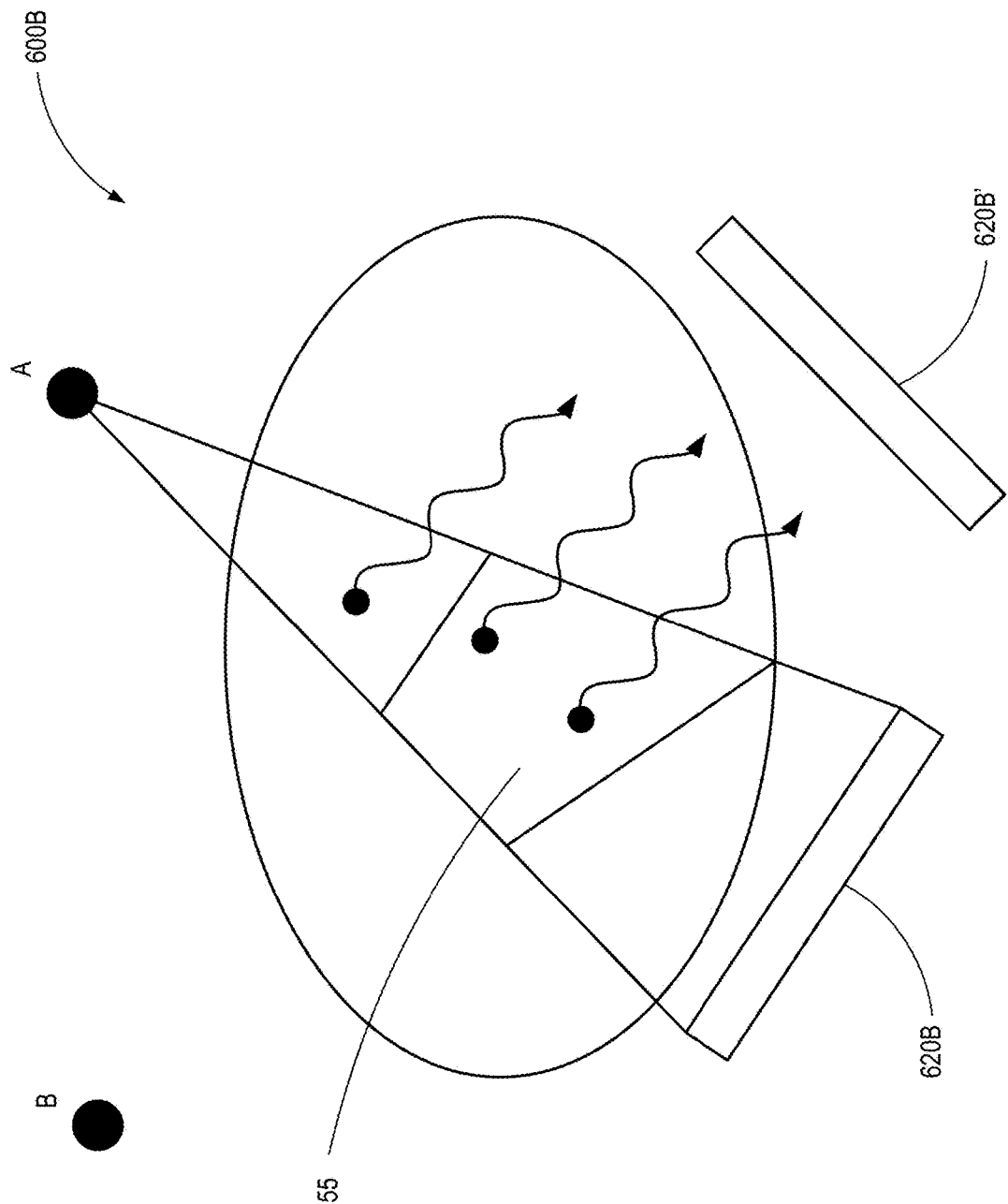

SYSTEMS AND METHODS FOR X-RAY TOMOSYNTHESIS IMAGE RECONSTRUCTION

RELATED APPLICATIONS

This application is a continuation of U.S. patent application Ser. No. 15/469,301, filed on Mar. 24, 2017, and titled "SYSTEMS AND METHODS FOR IMAGE RECONSTRUCTION", which is a continuation-in-part of U.S. patent application Ser. No. 14/198,390, filed on Mar. 5, 2014, and titled "IMAGING SYSTEMS AND RELATED APPARATUS AND METHODS", which claims the benefit under 35 U.S.C. § 119(e) of U.S. Provisional Patent Application No. 61/773,025, filed on Mar. 5, 2013, and titled "IMAGING SYSTEM" and also claims the benefit under 35 U.S.C. § 119(e) of U.S. Provisional Patent Application No. 62/313,041 filed Mar. 24, 2016 and titled "SYSTEMS AND METHODS FOR IMAGE RECONSTRUCTION." Each of the aforementioned applications is hereby incorporated by reference herein in its entirety.

STATEMENT REGARDING GOVERNMENT SUPPORT

This invention was made with government support under SBIR grant number 1456352 awarded by the National Science Foundation. The government has certain rights in the invention.

SUMMARY

Surgeons and interventional radiologists use medical imaging to guide their procedures, which procedures are referred to as Image Guided Interventions (IGI). In surgery, IGIs are most commonly performed with a C-arm.

A C-arm is an intra-operative x-ray system that creates real time 2D projection images. This imaging modality is called fluoroscopy. C-arms are popular because they are economical and their use does not lengthen the procedure time.

An alternative option is to use intra-operative 3D x-ray imagers. These 3D imagers include CT scanners, or Cone Beam CT (CBCT) scanners or C-arms. These systems provide 3D representations of the anatomy, which can be very valuable for complex anatomy or when precise 3D localization is important (e.g., for oncology and/or spine surgery). Such 3D images are static, and systems need to be coupled with navigation systems to mimic real-time imaging. Navigation systems can also be used with pre-operative imaging.

However, even though these 3D imagers provide superior visualization when compared to fluoroscopy, it comes with drawbacks. First, the complexity and time required for the procedure is lengthier. Further, intra-operative scanners enclose the patient and do not provide the surgeon with easy access to the anatomy being imaged and CBCT C-arms have moving parts that could interfere with patients, users, and/or bystanders (surgeons and staff).

Some of the methods, apparatus, and systems disclosed herein relate to intra-operative x-ray scanning. In some embodiments, these methods and systems can advantageously provide fast 3D reconstructions (in near real-time), which obviates the need for using surgical navigation systems. In some embodiments, the systems can have an open geometry that allows the user to access the anatomy during imaging, which can improve procedure workflow and/or integration with other systems. Some embodiments may alternatively, or additionally, be configured so as avoid having any exposed moving parts—i.e., any exposed parts that move during an imaging process that may expose patients, users, and/or bystanders to injury, for example.

In some embodiments, the system may comprise: a) a gantry for moving a plurality of radiation sources through one or more paths; and b) one or more radiation detectors, which may be configured to move or may be stationary relative to the patient and/or path(s). In some embodiments, one or more of the paths may comprise a continuous path. One or more of the paths may comprise, for example, a path on which a radiation source continuously moves in a single direction. Thus, a plurality of the paths of the plurality of radiation sources may overlap, wholly or in part. In other embodiments, one or more of the paths may be oscillating paths (i.e., the radiation source(s) oscillate along the one or more paths), and need not overlap with any of the other paths among the other radiation sources.

In other embodiments, a single moving radiation source may be provided. With respect to such embodiments, the moving radiation source may be configured to move within an enclosed source gantry or other such enclosure configured so as to avoid having any exposed moving parts during imaging. It should be understood, however, that one or more features or components of such a system may be configured to move between imaging sessions so as to, for example, allow for proper patient positioning. Such systems should still be considered as being configured to avoid having any exposed moving parts during imaging.

With respect to the source gantry, the detection device may be placed on the opposite side/hemisphere of the source gantry with respect to the patient. The system may further comprise c) a processor for repeatedly sampling the radiation detector(s) as the plurality of radiation sources move to generate the plurality of radiation absorption images for each radiation source; and d) a computer and computing program applying a reconstruction algorithm to the radiation absorption images to generate a 3 dimensional reconstruction of the object's region of interest. The computing program may be configured to update the 3 dimensional reconstruction (or information related/related to it). The system may further comprise e) a display or interface to provide the 3D dataset information (or information related/extracted from it) to a user.

A method can be performed to create a three-dimensional and time varying reconstruction of a region of interest of an object. In some implementations, the method may comprise acquiring radiation absorption images of the object region of interest by moving a plurality of radiation sources through one or more paths. The radiation absorption images may be acquired by one or more radiation detectors. The radiation detector(s) may be repeatedly sampled as the plurality of radiation sources move to generate a plurality of radiation absorption images for each radiation source. The projection geometry may be repeatedly obtained by the system (for example by using encoders and by "looking-up" previously obtained geometry calibration parameters).

An algorithm, such as a reconstruction and/or motion estimation and correction algorithm, may be applied to the radiation absorption images and associated projection geometries to generate a three-dimensional reconstruction of the object region of interest. In some implementations, the reconstruction algorithm may comprise an iterative reconstruction algorithm and/or a motion estimation and correction algorithm. The three-dimensional image may be updated as new radiation absorption images are acquired by the radiation detector(s) and the plurality of moving radiation sources. This image, at least a portion of this image, and/or data derived from or related to the imaging processing/analysis may be displayed to a user. In some implementations, this step may comprise displaying visual information derived from the three-dimensional reconstruction of an object region of interest on a display, such as a monitor.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

1. An imaging system for providing image reconstruction data of an object, the system comprising:
   an array of at least two radiation sources configured to move along a curved path substantially in a plane; and
   a detector not in the plane, the array configured such that the radiation sources emit radiation toward the detector in a sequence in which the emissions from each of the radiation sources occur at substantially the same frequency.
2. The system of Clause 1, wherein the curved path of the radiation sources is closed.
3. The system of Clause 2, wherein the curved path of the radiation sources is circular or elliptical.
4. The system of Clause 1, wherein the radiation sources move along the curved path.
5. The system of Clause 4, wherein the radiation sources oscillate along the curved path.
6. The system of Clause 4, wherein the radiation sources are configured to move along the curved path in a first direction and reverse direction to return toward their respective original locations.
7. The system of Clause 5, wherein the curved path of the radiation sources comprises an open curved path.
8. The system of Clause 7, wherein the radiation sources comprises four radiation sources and each of the four radiation sources moves along a separate open curved path that each have approximately a 90° arc.
9. The system of Clause 8, wherein the separate open curved paths collectively form a circle shape.
10. The system of Clause 8, wherein the separate open curved paths collectively form an elliptical shape.
11. The system of Clause 4, further comprising at least one gantry component housing the radiation sources, wherein the radiation sources move within the gantry component while the gantry component remains stationary relative to the detector.
12. The system of Clause 4, further comprising at least one gantry component housing the radiation sources, wherein the gantry component moves relative to the detector while the radiation sources remain stationary relative to the gantry component.
13. An imaging system for providing image reconstruction data of an object, the system comprising at least one radiation source that moves along a curved path within an enclosed gantry and emits radiation toward at least one detector, the detector not being coplanar with the curved path, the radiation source emitting radiation at at least two regions along the curved path.
14. The system of Clause 13, wherein the radiation source is configured to move from a first location along the curved path to a second location along the curved path and reverse direction at the second location to return to the first location.
15. The system of Clause 14, wherein the radiation source emits radiation along at least two regions along the curved path when moving toward the second location.
16. The system of Clause 14, wherein the curved path of the radiation source comprises an open curved path.
17. The system of Clause 13, wherein the curved path of the radiation source is closed.
18. The system of Clause 17, wherein the curved path of the radiation source is circular or elliptical.
19. An imaging system for providing reconstruction image data of an object and for allowing access to the object while imaging, the system comprising:
   at least one radiation source configured to move along a path formed by a first curve lying substantially along a first plane and a second curve lying out of the first plane;
   a radiation detector positioned and configured to receive radiation emitted from a radiation source with the object interposable therebetween; and
   a processor configured to receive radiation absorption data from the detector and apply a reconstruction algorithm.
20. The system of Clause 19, wherein the processor comprises two or more processors.
21. The system of Clause 19, wherein the second curve lies substantially in a second plane.
22. The system of Clause 19, further comprising generating a 3-D x-ray image using the radiation absorption data.
23. The system of Clause 22, wherein the 3-D x-ray image of the object is generated as the first radiation source moves along the path.
24. The system of Clause 22, further comprising a display for providing a visual representation of the 3-D x-ray image of the anatomy.
25. The system of Clause 19, further comprising a second radiation source configured to move along the path, spaced apart from the first radiation source.
26. The system of Clause 24, wherein the first and second radiation sources are positioned opposite each other along the path and move at the same speed.
27. The system of Clause 24, wherein the detector comprises first and second radiation detectors configured to move through a second path, the second path having a third curve lying substantially along a second plane and along a fourth curve lying outside of the second plane.
28. The system of Clause 19, wherein the path is generally a cylinder sine wave.
29. The system of Clause 19, wherein the path is generally a spherical sine wave.
30. The system of Clause 19, wherein the detector is stationary.
31. The system of Clause 19, wherein the detector moves along a second path in a position opposite the first radiation source such that radiation emitted from the first radiation source passes through the object toward the detector.
32. The system of Clause 19, further comprising an enclosed gantry for supporting the first radiation source.
33. The system of Clause 19, wherein the first radiation source is housed in a generally toroidal-shaped structure.
34. The system of Clause 19, wherein the first and second radiation sources are housed in separate structures.
35. The system of Clause 19, wherein the first and second radiation sources are rotatable through continuously changing angles.
36. The system of Clause 19, wherein the detector comprises separate first and second detectors.
37. The system of Clause 19, wherein the processor is configured to repeatedly sample the detector.
38. The system of Clause 19, wherein the path is continuous.

39. The system of Clause 19, wherein the path is discontinuous and the first radiation source moves around only a portion of the object.

40. A method for generating x-ray image data of an object, the method comprising:

moving a first radiation source along a path relative to the object, the path having a first curve lying substantially along a first plane and along a second curve lying out of the first plane; and recording projection images of the patient from different recording angles as the first radiation source moves along the path.

41. The method of Clause 40, wherein the second curve lies substantially in a second plane.

42. The method of Clause 40, wherein the first radiation source moves along a generally cylinder sine wave path.

43. The method of Clause 40, further comprising moving a second radiation source along the path and spaced apart from the first radiation source.

44. The method of Clause 40, wherein recording projection images comprises recording projection images at the same frequency.

45. The method of Clause 44, further comprising setting the first radiation source at a first energy level and the second radiation source at a second energy level.

46. The method of Clause 40, further comprising further comprising constructing a 3-D x-ray image, by a processor, from the projection images, wherein constructing a 3-D x-ray image comprises constructing a 3-D x-ray image from the subtraction projection images.

47. The method of Clause 46, further comprising subtracting projection images taken from substantially the same position at different times.

48. The method of Clause 46, further comprising subtracting projection images from substantially the same position at different energies.

49. The method of Clause 40, further comprising constructing a 3-D x-ray image, by a processor, from the projection images.

50. The method of Clause 48, further comprising updating the 3-D x-ray image as new subtraction projection images are produced.

51. The method of Clause 48, wherein constructing a 3-D x-ray image comprises applying multi-resolution techniques to provide a first 3-D image of a first resolution and a subsequent image of a resolution higher than the first resolution.

52. The method of Clause 48, further comprising displaying the 3-D x-ray image on the display.

In an example of an imaging system according to some embodiments of the invention, the system may comprise an x-ray tomosynthesis image reconstruction system configured to generate three-dimensional image data of at least an internal portion of a target object under a surface of the target object and a three-dimensional optical imaging system configured to reconstruct an image of at least a portion of the surface of the target object by generating surface three-dimensional image data. The optical imaging system may be registered to the x-ray tomosynthesis image reconstruction system. The system may further comprise a processor configured to apply an image reconstruction algorithm to generate a reconstructed three-dimensional image of the target object. The reconstruction algorithm may be configured to use the three-dimensional image data from the x-ray tomosynthesis image reconstruction system and to use surface three-dimensional image data from the three-dimensional optical imaging system as a constraint, such as a density constraint or geometric constraint, to improve image quality of the three-dimensional image data and reconstruct an image of the target object.

In some embodiments, the reconstruction algorithm may comprise an iterative reconstruction technique.

In some embodiments, the three-dimensional optical imaging system may further be configured to reconstruct an image of at least a portion of a surface of a surgical instrument or implant by generating surface three-dimensional image data for the at least a portion of the surface of the surgical instrument or implant. Thus, the density constraint may comprise at least in part a density profile derived from the surgical instrument or implant, and the reconstruction algorithm may be configured to apply the density profile of the surgical instrument or implant as a constraint to improve image quality of the three-dimensional image data.

In some embodiments, the system may be configured to apply a constraint of zero density from the surface three-dimensional image data. In some such embodiments, the target object may comprise a patient, and the constraint of zero density may be applied to a region outside of the at least a portion of the surface of the target object and outside of at least a portion of a surface of a surgical instrument.

In some embodiments, at least a portion of the constraint may be derived from an a priori, three-dimensional mass attenuation image registered to the at least a portion of the surface of the target object via surface registration.

In another example of an imaging system according to other embodiments, the system may comprise an x-ray tomosynthesis image reconstruction system configured to generate three-dimensional image data of a region of interest of a target object under a surface of the target object and a three-dimensional optical imaging system configured to generate surface three-dimensional image data of at least a portion of the target object. The optical imaging system may be registered to the x-ray tomosynthesis image reconstruction system, and the three-dimensional optical imaging system may be further configured to generate surface three-dimensional image data of a tool to be inserted into the region of interest of the target object, and to generate surface three-dimensional image data of the tool as the tool moves relative to the surface of the target object. The system may further comprise a processor configured to compile the surface three-dimensional image data of the tool over time and derive a trajectory of the tool relative to the target object and a display configured to display at least a portion of the region of interest and to dynamically display a trajectory of the tool relative to the region of interest.

In some embodiments, the tool may comprise a surgical instrument.

In some embodiments, the system may be configured to allow a user to select a preferred trajectory for the surgical instrument relative to the region of interest, and the processor may be configured to dynamically calculate a variance metric between the preferred trajectory and the trajectory.

In some embodiments, the display may be configured to display at least one of a number corresponding with the variance metric and an image illustrating both the trajectory and the preferred trajectory.

In some embodiments, the system may be configured to allow a user to select a target within the region of interest of the target object, and to dynamically display a distance between the tool and the target.

In some embodiments, the imaging system may be configured to dynamically adjust the region of interest in response to movement of the tool.

In some embodiments, the imaging system may be configured to dynamically define the region of interest so as to contain a point adjacent to a distal tip of the tool. In some such embodiments, the imaging system may be configured to dynamically modify the display as the region of interest is defined by movement of the distal tip of the tool.

In an example of a four-dimensional imaging system according to some embodiments, the system may comprise an x-ray tomosynthesis image reconstruction system configured to generate three-dimensional image data of at least a portion of a target object and a tracking system configured to track movement of the at least a portion of the target object and generate motion data for a motion model based upon movement of the at least a portion of the target object. A processor configured to generate a reconstructed three-dimensional image of the at least a portion of the target object over time comprising four-dimensional image data may also be provided. The reconstruction algorithm may be configured to use the three-dimensional image data from the x-ray tomosynthesis image reconstruction system and to use motion data from the tracking system to generate the four-dimensional image data.

In some embodiments, the motion model may comprise use of a rigid transformation.

In some embodiments, the tracking system may comprise a three-dimensional tracking system. In some such embodiments, the tracking system may comprise a three-dimensional imaging system. The three-dimensional imaging system may be configured to use the motion data from the three-dimensional imaging system to generate movement of the reconstructed three-dimensional image.

In some embodiments, the x-ray tomosynthesis image reconstruction system may be further configured to generate motion data based upon movement of the at least a portion of the target object, and the imaging system may be configured to combine the motion data from the tracking system with the motion data from the x-ray tomosynthesis image reconstruction system to generate movement of the reconstructed three-dimensional image.

In yet another example of an imaging system according to some embodiments, the system may comprise a three-dimensional tracking system configured to generate a first data layer comprising motion data of a tool or implant in motion with respect to a target object and an x-ray tomosynthesis imaging system configured to obtain projective image data of at least a portion of the target object and the tool or implant in motion with respect to the target object. The three-dimensional tracking system may be registered to the x-ray tomosynthesis imaging system. The system may further comprise a processor configured to generate a second data layer from the three-dimensional tracking system and from the projective image data from the x-ray tomosynthesis imaging system. In some embodiments, the processor is configured to use a reconstruction algorithm to reconstruct the first data layer and the second data layer individually, each data layer having different constraints, and the processor may be further configured to combine the first data layer with the second data layer to generate a reconstructed three-dimensional image of at least a portion of the target object with the tool or implant.

In some embodiments, the three-dimensional tracking system may be configured to identify the tool or implant using an a priori density profile, and the three-dimensional tracking system may be further configured to use a derived density profile based on the tool or implant to improve the reconstruction of the second data layer and thereby improve the reconstruction of the three-dimensional image.

In some embodiments, the three-dimensional tracking system may comprise a three-dimensional optical imaging system configured to generate the motion data by tracking movement of the tool or implant.

In some embodiments, at least one of a shape and a color of the tool or implant may be used to identify the tool or implant using an a priori density profile and a derived density profile based on the tool or implant to improve the reconstruction of the second data layer and thereby improve the reconstruction of the three-dimensional image.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 6A is a schematic depiction of yet another embodiment of an imaging system.

FIG. 6B is a schematic depiction of still another embodiment of an imaging system.

DETAILED DESCRIPTION

Figure 1:
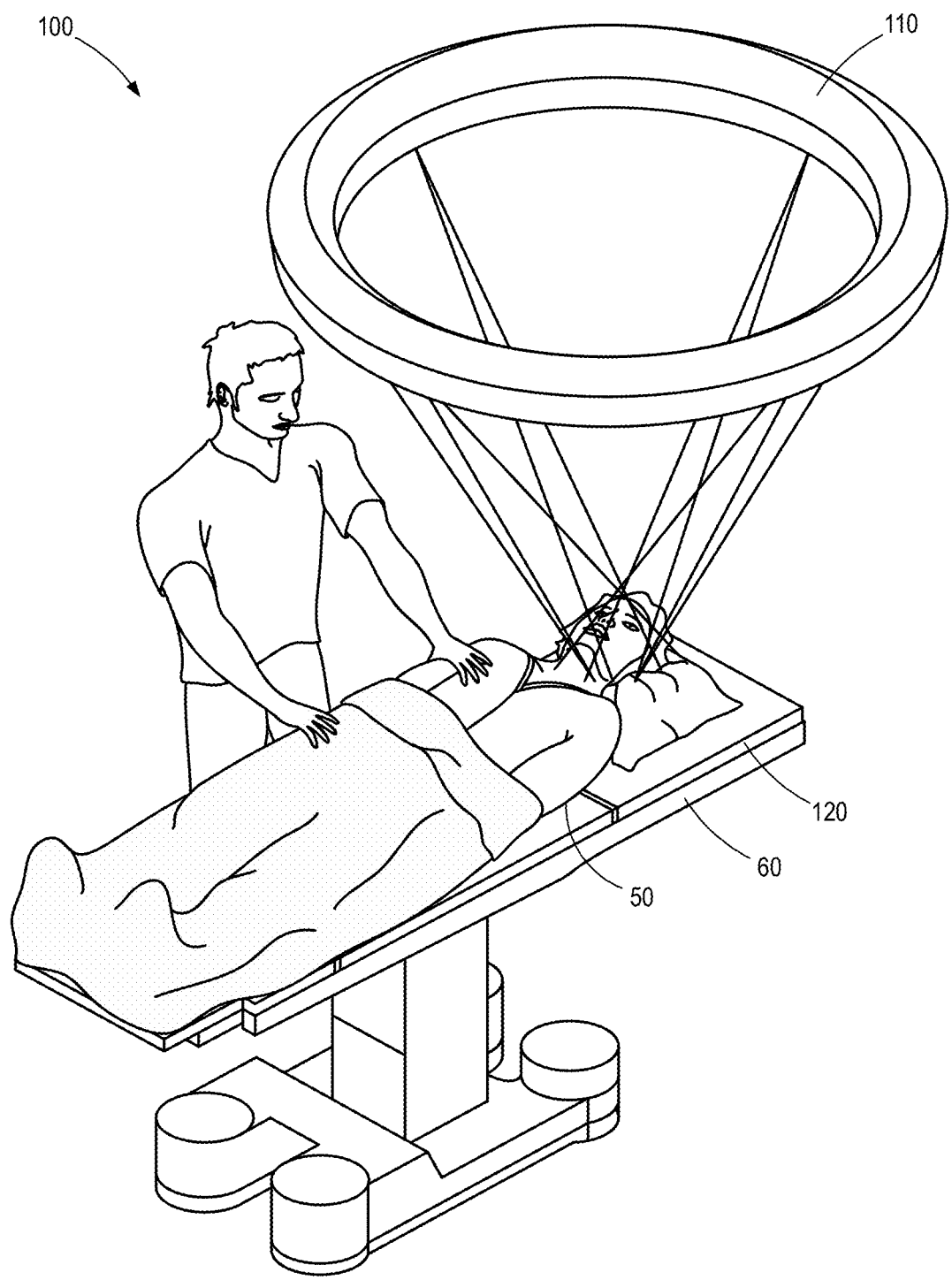
FIG. 1 is a perspective view of an embodiment of an imaging system.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Disclosed herein are various embodiments and implementations of apparatus, methods, and systems for providing imaging data. In some embodiments, the system can use multiple radiation sources that move substantially along a path or trajectory. The use of multiple radiation sources can increase the speed at which the system can acquire projections from the full path, which can reduce acquisition time and latency of the updates.

Various additional embodiments of apparatus, methods, and systems are disclosed herein that relate to image reconstruction and/or image reconstruction enhancement, such as, in some embodiments and implementations, using tracking systems and/or cameras to enhance 3D and/or 4D reconstructions for image guidance, some of which may incorporate one or more elements of the x-ray imaging systems, such as the multiple, moving radiation sources previously mentioned.

The following terms shall be defined herein as follows:

Imaged object: an object or a collection of objects being imaged by an image reconstruction system.

Mass attenuation reconstruction: a method of determination of mass attenuation property of an imaged object over a volume.

Optical reconstruction: a method of determination of reflective surface of an imaged object.

3D x-ray image reconstruction system: a system that acquires x-ray projection images and performs mass attenuation and/or linear attenuation reconstruction over an imaging object.

3D optical image reconstruction system: a system that acquire optical images and performs optical reconstruction over an imaging object.

Tracking system: a system that provides position and/or orientation of objects with respect to a reference frame.

In some embodiments, the radiation source(s) can move substantially along a path(s) or trajectory(ies) that can be circular in a common plane. The path(s) or trajectory(ies) can also be substantially along a cylinder sine wave or saddle-shaped path, a spherical sine wave, a hyperbolic paraboloid path, or other three-dimensional paths or trajectories. Other paths can be straight or linear along at least a portion of the extent. The path(s) can have multiple peaks and valleys, such as 2 peaks and 2 valleys (as along the brim of a saddle, for example), 3 peaks and valleys, 4 peaks and valleys, 5 peaks and valleys, etc. Further, some embodiments can be configured such that the path(s) undulates with variable amplitude or height peaks and valleys. The path(s) can traverse or extend into and out of and/or at least partially within a plane that passes through the object to be images. The path(s) can be curved in one or more planes. The path(s) can have a continuous curve or bend. In some embodiments, the path(s) can be discontinuous, such as an open curved path, extend along less than an entire circumference of a target space or object, or incompletely surround the target space or object. For example, an open curved path can comprise a beginning point that is separate or spaced apart from its end point, such as a 90 degree arc of a circle or ellipse. The path(s) can define one or more corners, sharp turns, or discontinuities. Multiple separate paths can be used for multiple separate sources and/or detectors with one or more sources and/or detectors moving along the multiple separate paths.

In some embodiments, one or more of the paths of the one or more radiation sources may be configured to at least substantially match one or more of the paths of the one or more radiation detectors. In some such embodiments, for example, the source path or paths may have the same shape (not necessarily the same size) as the detector path. In certain preferred embodiments, the radiation sources are configured to move at the same angular speed relative to the detection sources such that each source is positioned at a location that corresponds with a location of the detector at a given moment in time. Thus, in embodiments, in which one path is larger than the other, for example, the source(s) and/or detector(s) on the larger path will move faster (but at the same angular or rotational speed) than the source(s) and/or detector(s) on the smaller path.

In other embodiments, the detector(s) may be stationary relative to the patient and/or path(s). The system can comprise two or more paths for at least one radiation source and/or at least one radiation detector.

In some embodiments, the system may comprise one or more paths above a target space and one or more paths below the target space for at least one radiation source and/or at least one radiation detector.

For example, the system may comprise at least one radiation source and/or at least one radiation detector in a path above the target space, with at least one radiation source and/or at least one radiation detector below the target space. In other embodiments, the system may comprise at least one radiation source and/or at least one radiation detector in two paths below the target space, along with another at least one radiation source and/or at least one radiation detector in two paths above the target space.

In some embodiments, the system can have radiation sources that rotate thereby allowing the system to work with a finite/small number of sources and still have coverage in terms of angular density (for example, in projections per degree), which is needed to have good image reconstruction quality.

Further, in some embodiments, the system can use a source gantry that is separate and on the opposite side of the patient versus the detection device in order to provide the user with access to the patient's anatomy. For example, the system can provide access for the user by approaching the anatomy between the gantry and the detection device and also provide compatibility with surgical tables. In other examples, the system can provide access for the user to the anatomy above the gantry and/or the detection device. In such embodiments, the system can comprise a track.

The separation in two hemispheres (one for radiation sources, one for detection device) makes the mathematical problem of solving for the 3D image (also called image reconstruction) ill posed. Thus, computer intensive iterative algorithms (based on iterative forward and back projections) that use regularization (typically an a priori constrain that helps the algorithm converge) may be used during such image reconstruction.

Further, in some embodiments having multiple rotating detectors, the detectors that are not observing the projected image may be used to observe backscatter x-ray. The backscatter x-ray can be used to improve the quality of the reconstruction, for example, by changing dynamically the regularization function.

FIG. 1 illustrates an embodiment of an imaging system 100 comprising a gantry 110. Gantry 110 comprises a circular gantry configured to contain and/or house one or more moving radiation sources. The term "gantry," as used herein, should be understood to encompass any structural element configured to position various radiation sources and/or detectors within a suitable location for imaging. Gantry 110 further comprises an enclosed gantry configured to avoid having any exposed moving parts—i.e., any exposed parts that move during an imaging process that may expose patients, users, and/or bystanders to injury, for example. Thus, each of the radiation sources (not shown) contained within gantry 110 are configured such that no moving parts that facilitate such movement are exposed outside of gantry 110.

Imaging system 100 further comprises a detector 120, which may comprise a flat panel detector. Detector 120 may further comprise a stationary single digital detector.

Gantry 110 may house one or more radiation sources, such as x-ray sources for example, that extend substantially along a path. The path can be any of a variety of shapes, as discussed above. FIG. 1 illustrates one possible configuration in which the detector 120 is positioned under the patient and the gantry 110 is positioned over the patient 50. Gantry 110 may be configured itself to rotate, thereby rotating the one or more radiation sources contained therein/thereon. Alternatively, the one or more radiation sources may be configured to be moved independently of a stationary gantry 110.

As illustrated in FIG. 1, gantry 110 may be configured to move the one or more radiation sources in a circular or elliptical path above the bed 60 on which the patient 50 lies. The circular or elliptical path may be in a single plane if desired. Further, one or more detector panels, such as detector panel 120, may be positioned below the source(s) and the patient 50 to detect radiation emitted therefrom. As illustrated, the detector(s) 120 can be positioned on the bed below the patient. In alternative embodiments, however, the detector(s) may be positioned below the patient on or within a separate housing, or may be positioned above the patient, as described below.

In some embodiments, at least one of a) the gantry and b) the detector assembly can be hollow. Having a hollow element with a relatively small cross-section can allow the user to access the anatomy from the hollow portion of the source and/or detector by placing the hollow portion close to the patient, thereby eliminating or at least reducing the risk of direct x-ray beam exposure to the surgeon, providing compatibility with lighting during the procedure, and/or otherwise making the procedure more convenient and/or less risky.

In embodiments where the detector assembly is hollow it could be formed by a static detector (or assembled plurality of static detectors) or may comprise of a plurality of rotating detectors corresponding to one or more radiation sources. In some embodiments, the detector(s) may be positioned above the plurality of radiation sources. Such embodiments may be of great value because they may allow the x-ray or other radiation source to be beneath the patient and the detector above the patient, decreasing the scattered radiation to the surgeon (scatter radiation tends to "bounce back" towards the source, such as towards a surgeon's feet).

Figure 5:
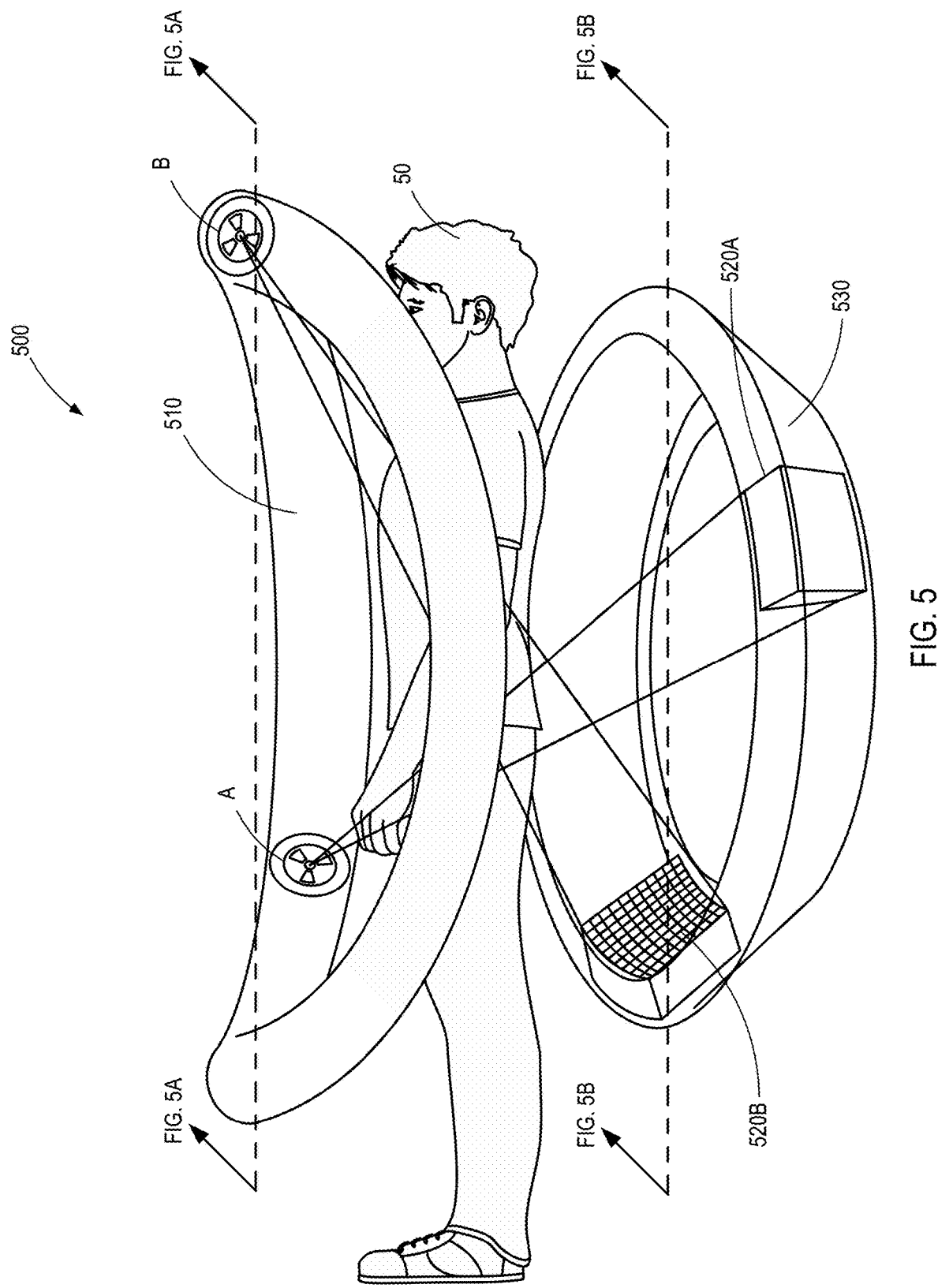
FIG. 5 depicts yet another embodiment of an imaging system.

In some embodiments where the source and detector gantries are close to the patient and the user accesses the anatomy from a central opening in a toroidal-shaped gantry or through another hollow portion of the system, the source and detector shapes may have a portion offset in the center along the patient axis as to allow simple positioning of the system along the axis of the patient during a procedure. An example of such a configuration is illustrated in FIG. 5, and will be discussed in greater detail in connection therewith.

As noted above, the emitting path or trajectory could be of any connected shape: oval or bean-like or 8-like. This reduces the possibility of the x-ray source to irradiate the surgeon and/or other bystanders, which are likely to be standing under the narrowing part of the 8 or bean-like shape.

Figure 2:
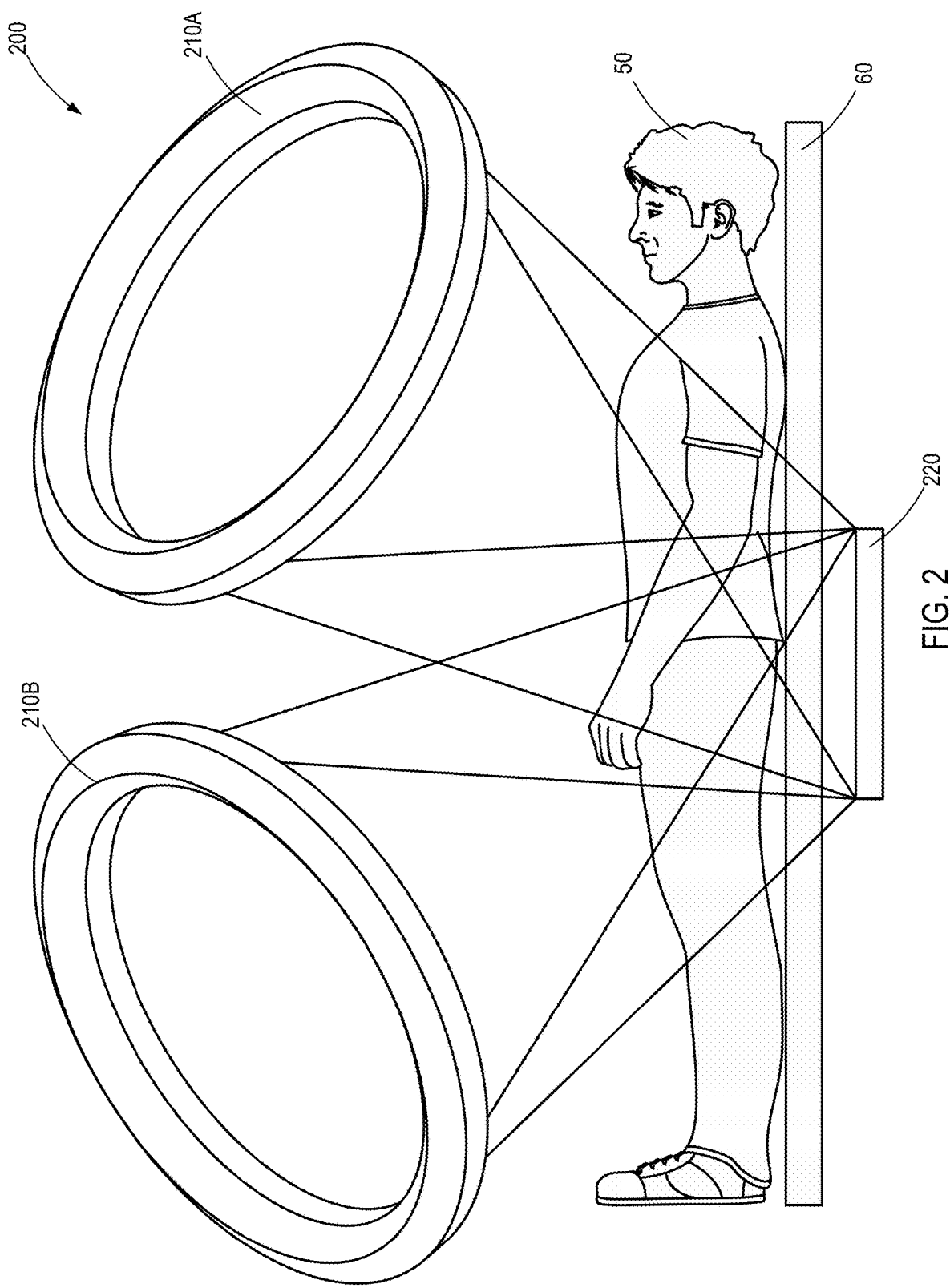
FIG. 2 depicts an alternative embodiment of an imaging system.

FIG. 2 illustrates an example of another imaging system 200. Imaging system 200 comprises two gantries, namely, gantries 210a and 210b, each of which comprises one or more radiation sources configured to move within a path defined by its respective gantry. In some embodiments, both gantries 210a and 210b comprise a plurality of moving radiation sources, such as moving x-ray sources. As mentioned above, in some embodiments, the radiation sources may be stationary relative to the gantry, in which case the gantry may be movable. Alternatively, gantry may be configured to guide the radiation source(s) which may move within a path defined by the gantry.

One or both of gantries 210a and 210b may comprise radiation sources that move within the full curved path (in some embodiments, circular) defined by their respective gantry. Alternatively, one or both of gantries 210a and 210b may be configured such that their respective radiation source(s) move within a path only partially-defined by their respective gantry.

System 200 further comprises a detector 220 comprising a flat panel positioned below table 60 (and below patient 50). As illustrated in FIG. 2, gantries 210a and 210b may each be angled inwardly towards detector panel 220. In other words, detector panel 220 may be positioned along an axis at least substantially parallel to the axis of patient 50, gantry 210a may be angled in a first direction with respect to such axis, and gantry 210b may be angle in a second, opposite direction with respect to such axis. In some embodiments, one or both of gantries 210a and 210b may comprise a dimension, such as a diameter in the case of circular gantries, that is at least substantially equal to a dimension of detector 220.

Figure 3A:
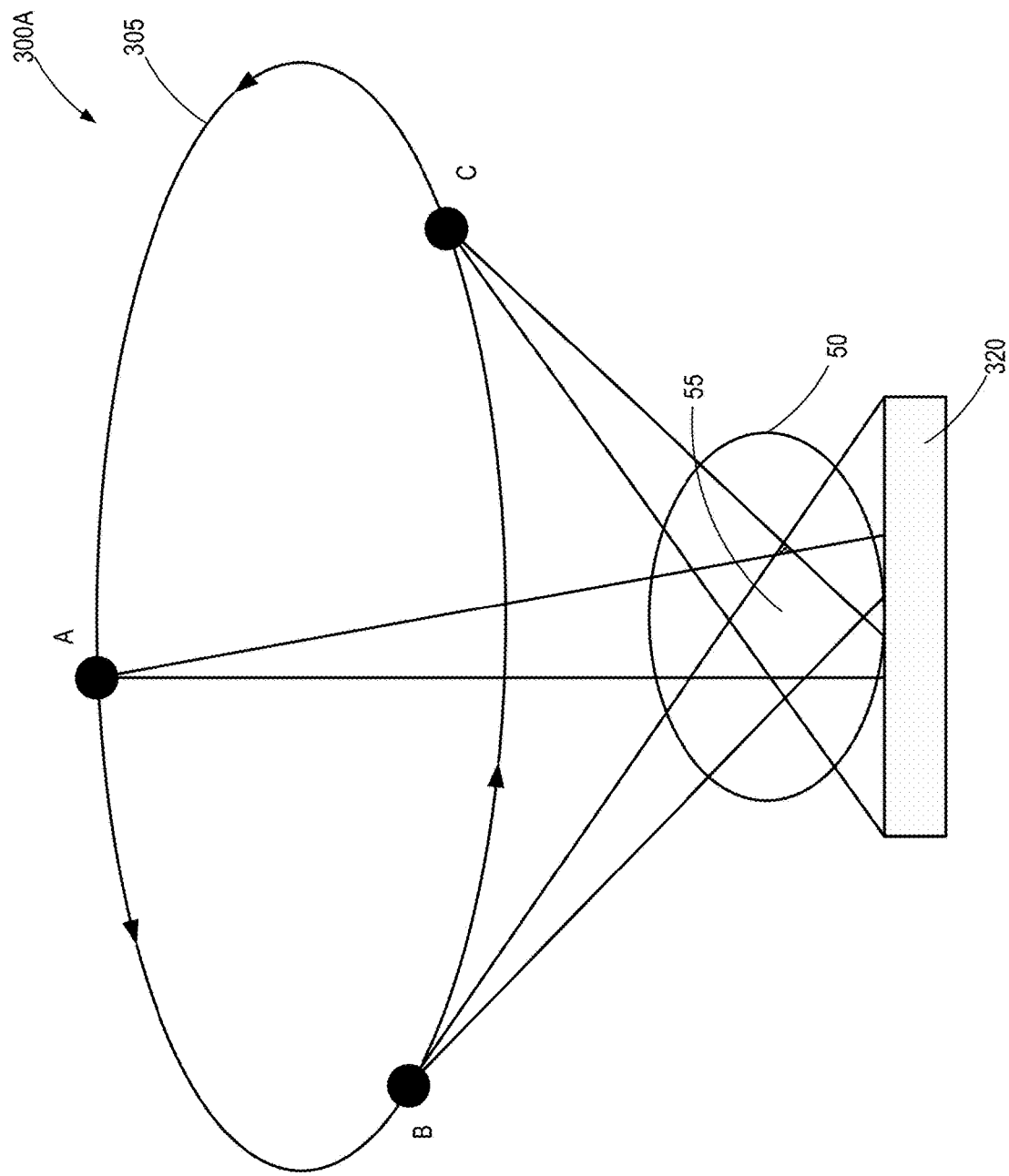
FIG. 3A is a schematic depiction of an alternative embodiment of an imaging system.
Figure 3B:
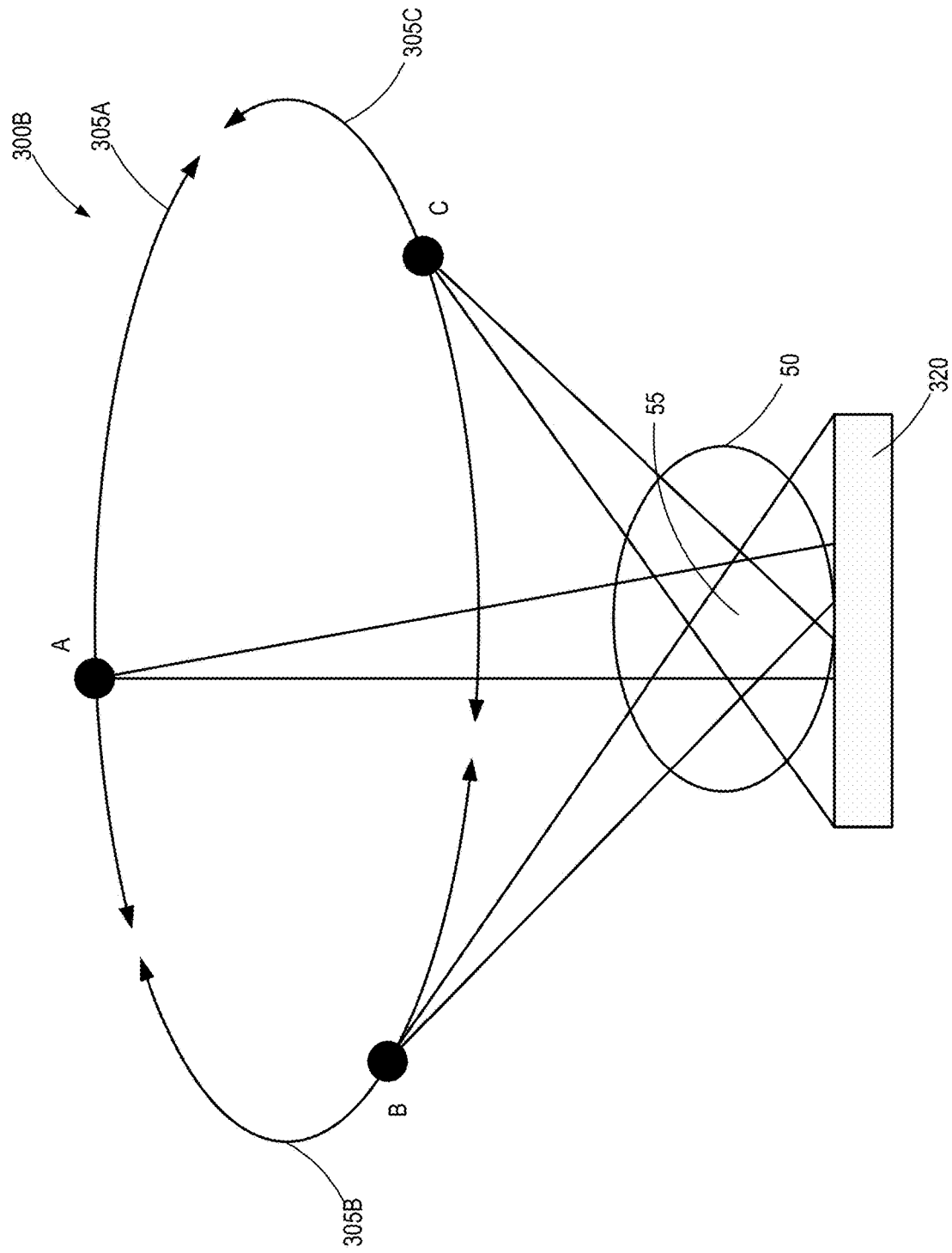
FIG. 3B is a schematic depiction of another alternative embodiment of an imaging system.

FIGS. 3A and 3B illustrate schematics for another embodiment of an imaging systems 300A and 300B, respectively, comprising three moving radiation sources. FIG. 3A illustrates a system 300A comprising three moving radiation sources, namely, sources A, B, and C, that each move along a single circular path 305. Preferably each of these sources moves at at least substantially the same speed and in the same direction along path 305 (as illustrated by the arrows) such that the distance between each source remains constant.

As also illustrated in FIG. 3A, each of the various sources (although three are illustrated in the figure, any number of sources may be used as desired) may emit x-ray or other radiation towards a detector 320, such as a digital flat panel detector or other such detector. The intersection between a particular radiation source, a portion of a patient 50's anatomy, and the detector 320 may allow for reconstruction of a particular volume 55 of the patient anatomy. By moving the sources around path 305, various projections of the anatomy of patient 50 may be taken from various directions and used to provide a three-dimensional reconstruction of a volume of the anatomy as desired.

In the embodiment depicted in FIG. 3A, each of the various sources may be configured to move along the same path 305 (although obviously at different points along path 305 at any given moment), as indicated by the arrows in this figure. However, various other embodiments are contemplated. For example, as previously mentioned, a variety of other numbers of sources may be used as desired. In fact, although at least two sources is preferred for certain embodiments, other embodiments may comprise a single radiation source, as described in greater detail below.

In addition, in other embodiments, each of the various radiation sources, or at least a subset of the radiation sources, may occupy separate moving paths. For example, FIG. 3B illustrates an embodiment similar to FIG. 3A except that the three radiation sources (A, B, and C) oscillate along independent paths. More particularly, source A oscillates between opposite ends of curved path 305A, source B oscillates between opposite ends of curved path 305B, and source C oscillates between opposite ends of curved path 305C, as indicated by the respective arrows on these paths.

As also illustrated in FIG. 3B, the combined trajectories of the various paths 305A, 305B, and 305C at least substantially matches the shape of the single path 305 of the embodiment of FIG. 3A. Again, however, a wide variety of other numbers of oscillating paths may be employed for a wide variety of other numbers of radiation sources as desired. For example, two radiation sources may be employed, in which case, assuming the sources are configured to oscillate, they may oscillate between respective paths defining semicircles that together define a circular path. Of course, in some embodiments, technically the collective paths of the various sources may not precisely touch one another for practical reasons. However, a configuration substantially in the form depicted in FIG. 3B may be considered to comprise a plurality of individual source paths substantially defining a collective, circular path even though there may be small gaps between the various paths.

As those of ordinary skill will appreciate, the source path(s), whether being a single path for a plurality of sources or a collective path defined by a plurality of paths taken by individual sources, may alternatively comprise other shapes and/or sizes, depending upon the desired application. Moreover, some embodiments may be configured to allow for reconfiguring one or more of the source paths in order to, for example, accommodate differing patients and/or anatomical structures/features to be imaged.

However, certain preferred embodiments comprise at least a plurality of radiation sources moving along one or more paths. Such path(s) may be closed in some such embodiments. Having multiple sources may be useful to increase the speed, angular coverage, and/or efficiency at which images, such as adsorption images, may be acquired. This may allow for reduced acquisition time and/or latency of imaging updates.

In addition, it should be understood that although certain preferred embodiments comprise curved radiation source paths, in other embodiments, one or more of the source paths may be linear. In some such embodiments, the collective path defined by all of the radiation source paths may comprise a polygon. In some such embodiments, such a polygon may approximate a curved path, such as a circle.

The system 300B, like system 300A, further comprises a detector 320, which may comprise a flat panel detector. The intersection between a particular radiation source, a portion of a patient 50's anatomy, and the detector 320 may allow for reconstruction of a particular volume 55 of the patient anatomy. In addition, having the sources, which may be arranged in, on, or otherwise coupled with a gantry, separate from and on an opposite side of a patient compared to the detector may provide the user with access to the anatomy by approaching the anatomy between the gantry and the detector and may also provide compatibility with surgical tables, chairs, and the like.

The firing/detecting sequence of the various radiation sources and detectors may also vary as desired. For example, in some embodiments, the sequence may be sequential. In other words, each source may emit radiation and then be detected by a detector sequentially to provide an image. In some such embodiments, each source that has been fired/emitted may be detected prior to another source, such as an adjacent source, emitting radiation.

Alternatively, the sequence may be parallel. In other words, a plurality of sources may emit radiation simultaneously, or at least substantially simultaneously, and then be read together by the detector.

Figure 4:
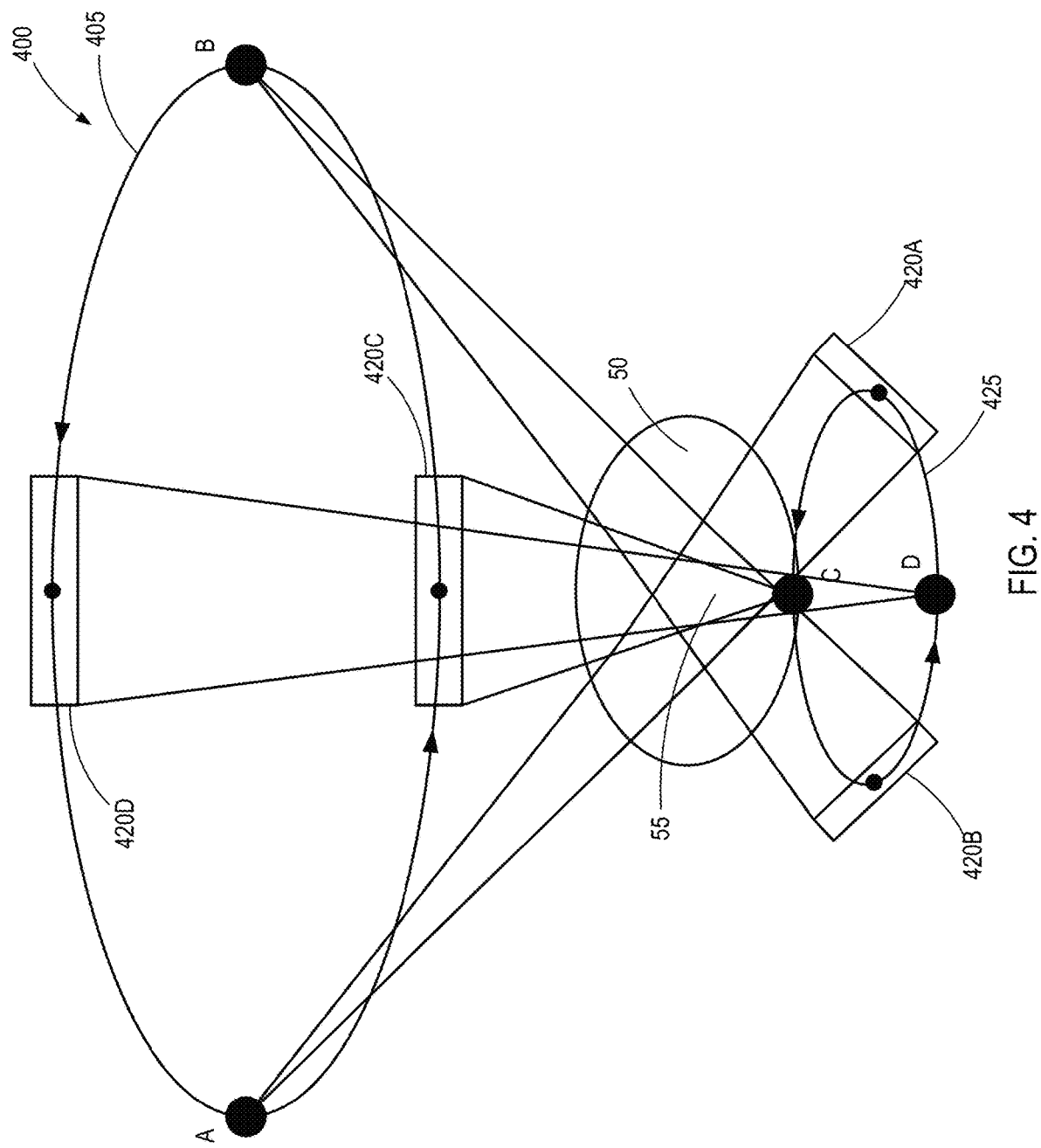
FIG. 4 is a schematic depiction of still another embodiment of an imaging system.

FIG. 4 illustrates an alternative embodiment of an imaging system 400 comprising moving radiation sources and moving detectors. As illustrated in this figure, two radiation sources A and B are configured to move in a curved path 405. Path 405 may define, for example, a circular or oval shape. Radiation sources A and B may be positioned in, on, or otherwise coupled with a gantry, as previously mentioned. Such gantry may be positioned on a first side of a patient 50.

On a second side of patient 50 opposite from the first side, detectors 420A and 420B may be positioned to move along a similar path 425. In some embodiments, path 425 may have a similar, or identical, shape and/or size as path 405. Detectors 420A and 420B may comprise flat panel detectors. In some such embodiments, detectors 420A and 420B may be tilted or angled inwardly relative to patient 50, which may be useful to assist in increasing the reconstructed volume of an image of an anatomical structure or feature.

In some embodiments, detectors 420A and 420B may move in the same direction as sources A and B. Alternatively, detectors 420A and 420B may move along path 425 in an opposite direction with respect to the direction in which sources A and B move within path 405.

In some embodiments, the detectors 420A and 420B may be positioned in a horizontal direction relative to a plane and/or axis of the patient 50 and/or path 405. In some such embodiments, the detectors and sources may be synchronized to allow for direct firing of radiation onto a detector. For example, the detector may be positioned such that the radiation will hit the detector at a perpendicular, or at least substantially perpendicular, angle with respect to the detector (assuming the detector comprises a panel or is otherwise flat).

Some embodiments may comprise a combination of sources and detectors configured to move along the same path. For example, system 400 may also comprise two additional detectors 420C and 420D interspersed with sources A and B that are configured to move in path 405. Detectors 420C and 420D may be configured to receive radiation from sources C and D, which may be configured to move in path 425 along with detectors 420A and 420B.

As yet another alternative, in some embodiments, the detector(s) may be positioned above the patient/anatomy and the sources may be positioned below the patient/anatomy. This may be useful for certain applications to, for example, provide less x-ray or other radiation scatter to the upper part of surgeons or bystanders.

FIG. 5 illustrates an alternative embodiment of an imaging system 500 comprising a plurality of moving radiation sources and a detector. System 500 comprises a first enclosure 510 defining a path for two moving radiation sources A and B. System 500 further comprises a second enclosure 530 for a corresponding number of detectors 520A and 520B. A patient 50 may be positioned in between the radiation sources and the detectors. Although detectors 520A and 520B are depicted as being curved and having a curvature at least substantially matching that of enclosure 530, it should be understood that other embodiments are contemplated in which the detectors 520A and 520B comprise flat panel detectors.

As depicted in FIG. 5, enclosure 510 may be shaped to define a path for sources A and B that is non-planar. More particularly, enclosure 510 may be configured in a "saddle" shape or otherwise may comprise a valley or other such offset region to allow for a patient to be partially positioned within this region. This may improve access to certain anatomical regions and/or may improve image quality.

Similarly, as also depicted in FIG. 5, the detector enclosure 530 may comprise a similar shape oriented in an opposite direction to allow for closer approximation of one or more sources and one or more detectors at a particular moment in time.

In some embodiments, a rail system may be positioned within one or both of enclosures 510 and 530 so as to move sources A, B and/or detectors 520A, 520B. In alternative embodiments, one or both such enclosures may instead comprise a shape that extends along an axis or a plane (or extends at least substantially parallel to a plane). In other words, the "valley" referenced above may be omitted. In some such embodiments, enclosure 510 may be part of a rotating gantry if desired. In some embodiments, one of the detector(s) and source(s) may be configured to move and one may be stationary. For example, in some embodiments, sources A, B may be configured to move within one or more predefined paths and one or more stationary detectors may be used to receive radiation from such source(s).

Figure 5A:
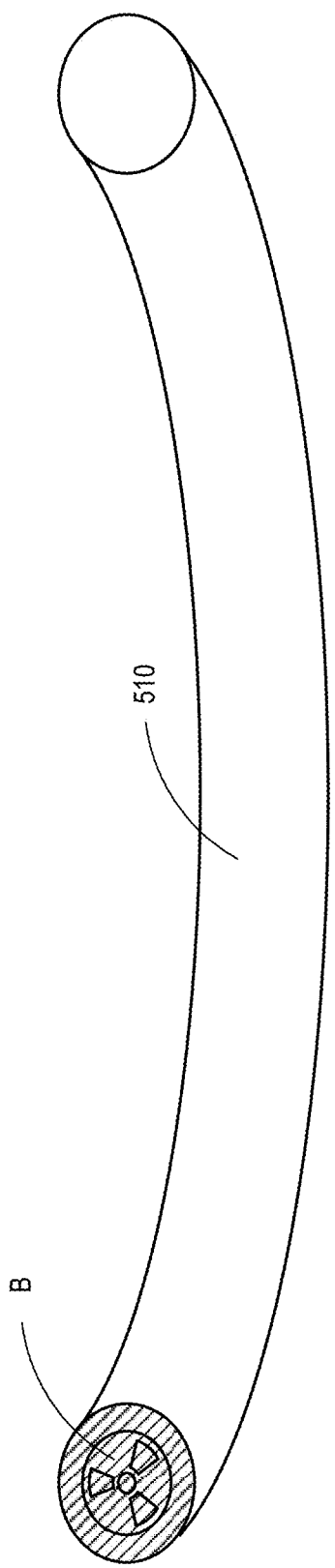
FIG. 5A is a cross-sectional view taken from line 5A-5A in FIG. 5.
Figure 5B:
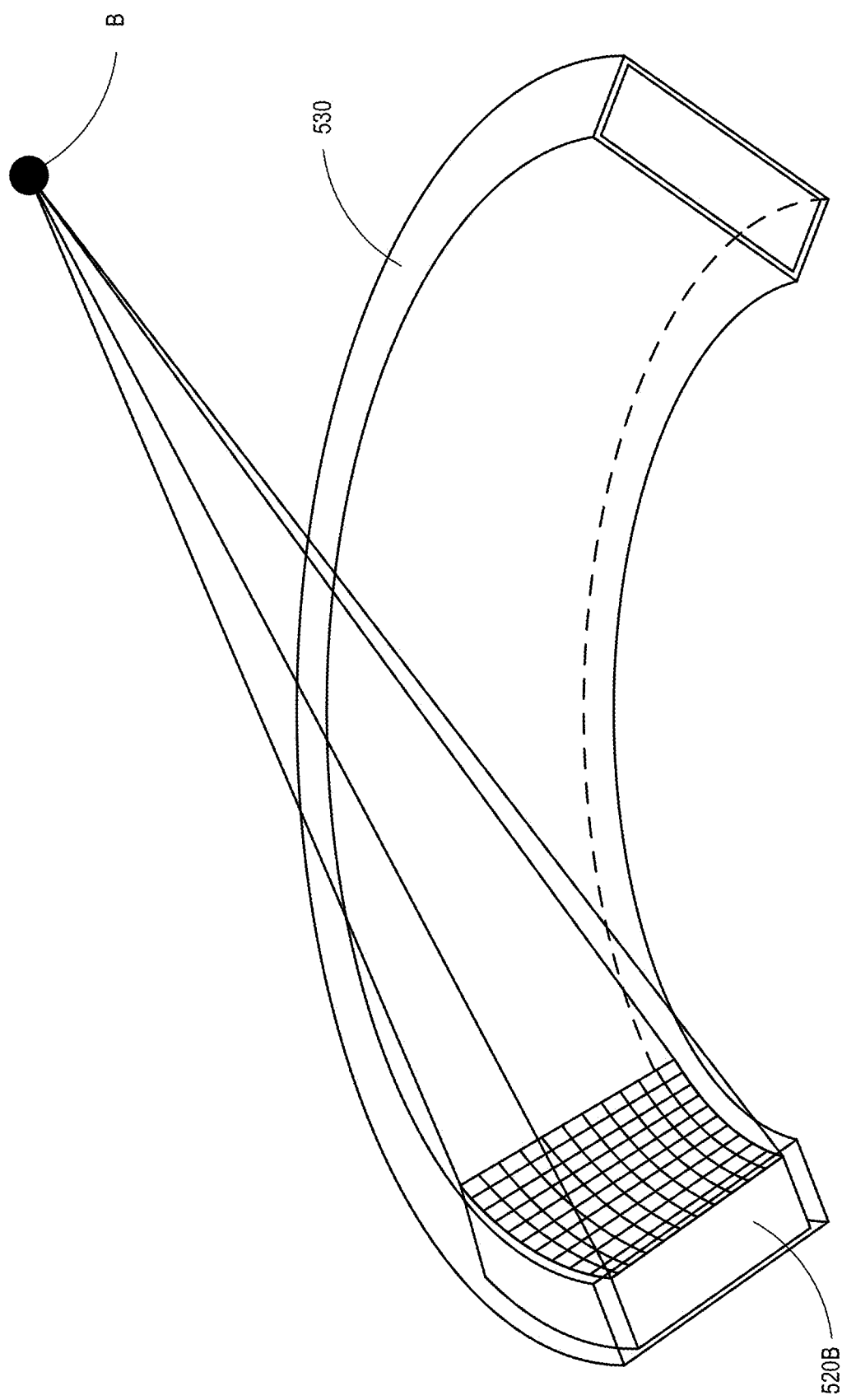
FIG. 5B is a cross-sectional view taken from line 5A-5B in FIG. 5.

FIGS. 5A and 5B are partial cross-sectional views of examples of structures from system 500 that may be used to house, contain, and/or otherwise facilitate the positioning and/or movement of radiation sources and/or radiation detectors. FIG. 5A depicts a toroidal enclosure 510. In some embodiments, toroidal enclosure 510 may be part of a gantry configured to position enclosure 510 above (or, in other embodiments, below) a patient to facilitate imaging of one or more anatomical structures positioned within a central opening, for example, of the enclosure 510. Although in some embodiments enclosure 510 may be positioned at least substantially parallel to a plane along its entire length, other embodiments may comprise a valley or saddle shape, as shown in FIG. 5.

FIG. 5B is a partial cross-sectional view of another structure or assembly 530 for housing, containing, and/or otherwise facilitating the positioning and/or movement of one or more radiation detectors. As shown in this figure, like enclosure 510, structure 530 may also comprise an enclosure. However, enclosure 530 comprises a rectangular cross-sectional shape. It is contemplated, however, that in other embodiments, enclosure 530 may comprise other shapes, and the structure(s) associated with the radiation source(s) may be similar or identical in shape and/or size to the structure(s) associated with the radiation detector(s) if desired. For example, in some embodiments, the detector assembly 530 may comprise a saddle shape either alternatively to, or in addition to, the gantry or assembly for the radiation source(s).

As previously mentioned, structure 530 may be configured to house moving radiation detectors, such as detectors 520A and 520B, if desired. Alternatively, structure 530 may be configured to house one or more stationary detectors.

As also shown in FIG. 5B, in some embodiments, structure 530 may be configured to angle the detector(s) housed therein or otherwise coupled therewith in a direction to further facilitate imaging. For example, in the depicted embodiment, structure 530 is configured to angle detectors 520A and 520B away from one another. This angling also directs the detecting faces of these detectors towards enclosure 510, which allows for radiation from one or more sources contained therein to be directed towards an intervening anatomical feature of interest and then towards one or more detectors.

In some embodiments, a first radiation source and a first radiation detector can form a first pair of devices. The system can have several pairs of devices. In some embodiments, the pairs of devices can be positioned and configured such that a source of a first pair and a detector of a second pair are positioned on the same side of a patient. The source and the detector can travel together along the same path, or at least along similar paths on the same side of the patient.

Each radiation source can be paired with and positioned opposite a respective radiation detector, such that each moves along the paths at corresponding rates of speed. For example, the sources can move at substantially the same rate of speed. However, in other embodiments, the source(s) may move at different rates of speed relative to the detector(s) or, as mentioned above, one of the source(s) and detector(s) may be stationary. Preferably, however, the source(s) at least move at the same angular speed as the detector(s).

FIGS. 6A and 6B schematically illustrate two alternative embodiments of imaging systems configured to provide additional imaging by way of backscatter imaging. System 600A comprises two radiation sources A and B and a single, flat panel detector 620A. As shown in FIG. 6A, a portion 55 of a patient's anatomy may be reconstructed by way of a transmission image 622A from source A and a backscatter image 624A also from source A. Backscatter images may be used to improve image reconstruction quality.

In some embodiments, the detector, such as detector 620A, may comprise an x-ray grid configured to only allow for x-ray transmission therethrough at one or more particular angles. This may be useful to filter scatter radiation from a transmission (or vice versa).

FIG. 6B illustrates an alternative embodiment of an imaging system 600B configured to provide both transmission and backscatter imaging. However, system 600B differs from system 600A in that it comprises two separate detectors, detector 620B and detector 620B'. Detectors 620B and 620B' are angled inwardly towards one another so as to face radiation sources A and B to facilitate imaging. In some embodiments, as previously discussed, detectors 620B and 620B' may be configured to move along with sources A and B. In other embodiments, detectors 620B and 620B' may be stationary.

At the moment of imaging depicted in FIG. 6B, a backscatter image of region 55 from source A is being received on detector 620B' and a transmission image of region 55 is being received on detector 620B. However, it should be understood that at other points during the operation of system 600B, detector 620B' may be receiving a transmission image and detector 620B may be receiving a backscatter image, depending upon the positioning/movement of the various sources and/or detectors during operation. It should also be understood that any number of radiation sources may be provided as desired. However, for certain embodiments comprising more than one radiation source, a sequential firing sequence may be needed.

Figure 7:
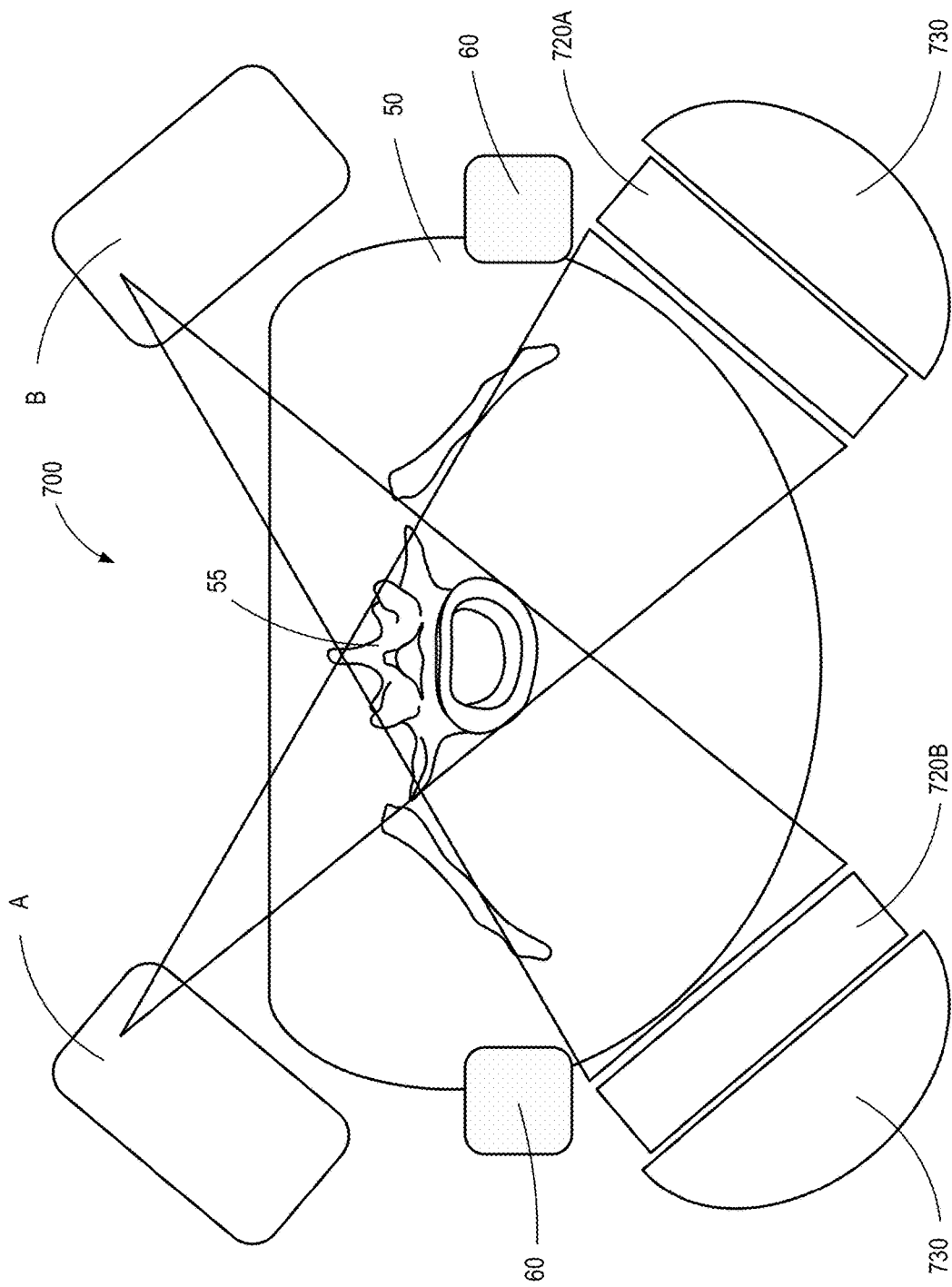
FIG. 7 depicts another embodiment of an imaging system.

FIG. 7 illustrates another embodiment of an imaging system 700. Imaging system 700 comprises four radiation sources and four detector panels. However, only two radiation sources and two corresponding detector panels are visible in the figure. More particularly, radiation sources A and B, which may be positioned above a prone patient 50, are shown in the figure. Radiation sources A and B may be configured to move in one or more paths above the patient 50 (on table 60) in order to provide an image of a portion 55 of an anatomical region of interest, such as a portion of a patient's spine for example. Two other radiation sources (not shown in FIG. 7) may similarly be configured to move about in the same or distinct paths in order to increase the imaging speed.

Two detector panels, namely, panels 720A and 720B, may also be provided below patient 50. In FIG. 7, detector panel 720A is receiving radiation from source A and detector panel 720B is receiving radiation from source B. Panels 720A and 720B are configured to be moved in one or more paths on one or more tracks 730. In the depicted embodiment, a single track is provided. However, other embodiments are contemplated in which multiple tracks may be provided. Also, although not shown in FIG. 7, two additional detector panels may be provided if desired. As shown in the figure, the various detector panels are angled inwardly towards one another so that they face towards a respective radiation source.

Figure 8:
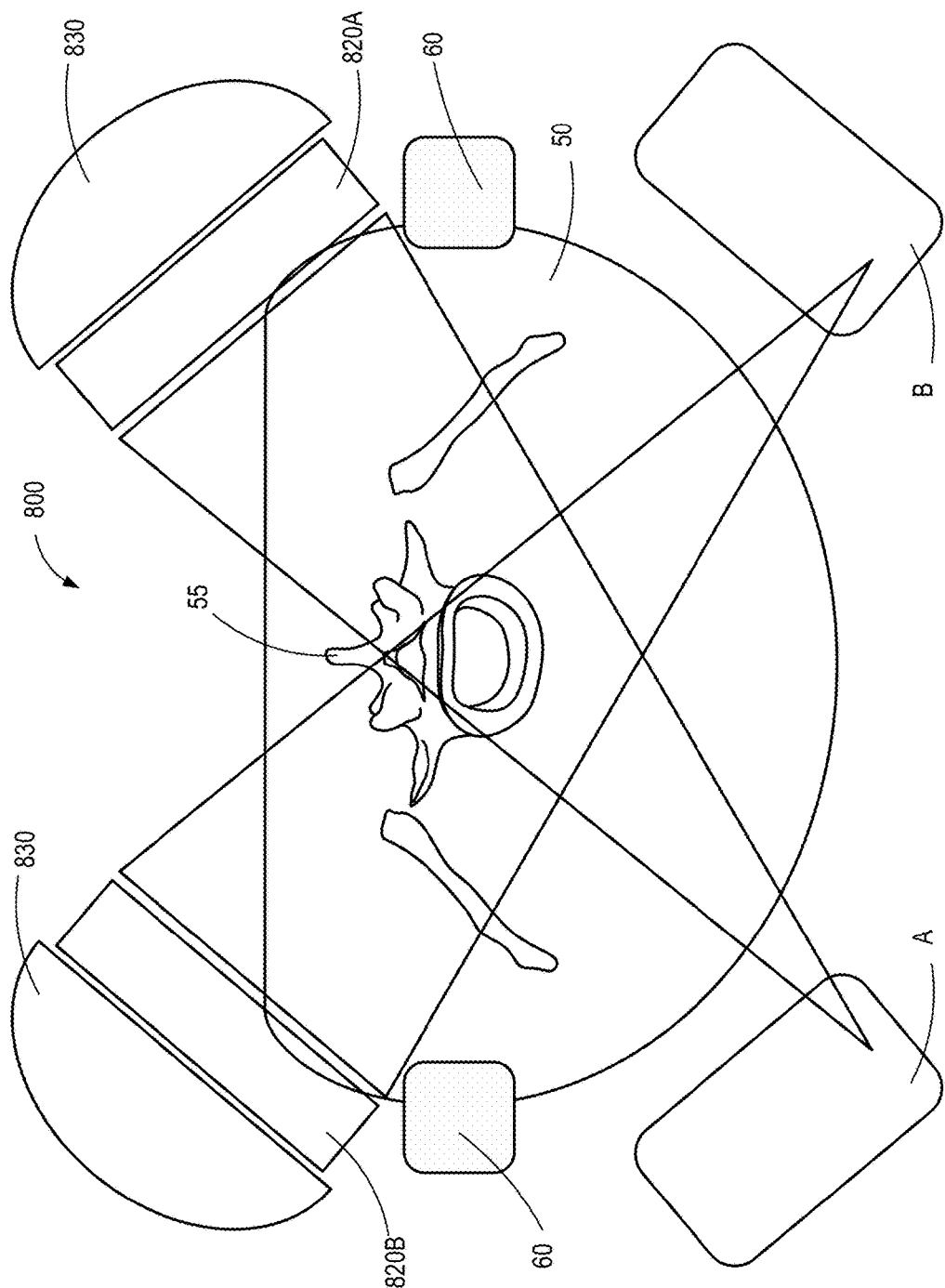
FIG. 8 depicts still another embodiment of an imaging system.

FIG. 8 illustrates yet another embodiment of an imaging system 800. Imaging system 800 is similar to imaging system 700 except that radiation sources A and B are positioned below a prone patient 50 and detector panels 820A and 820B, are positioned above patient 50. Like imaging system 700, imaging system 800 comprises one or more tracks 830 configured to move the various detector panels in one or more desired paths.

Figure 9:
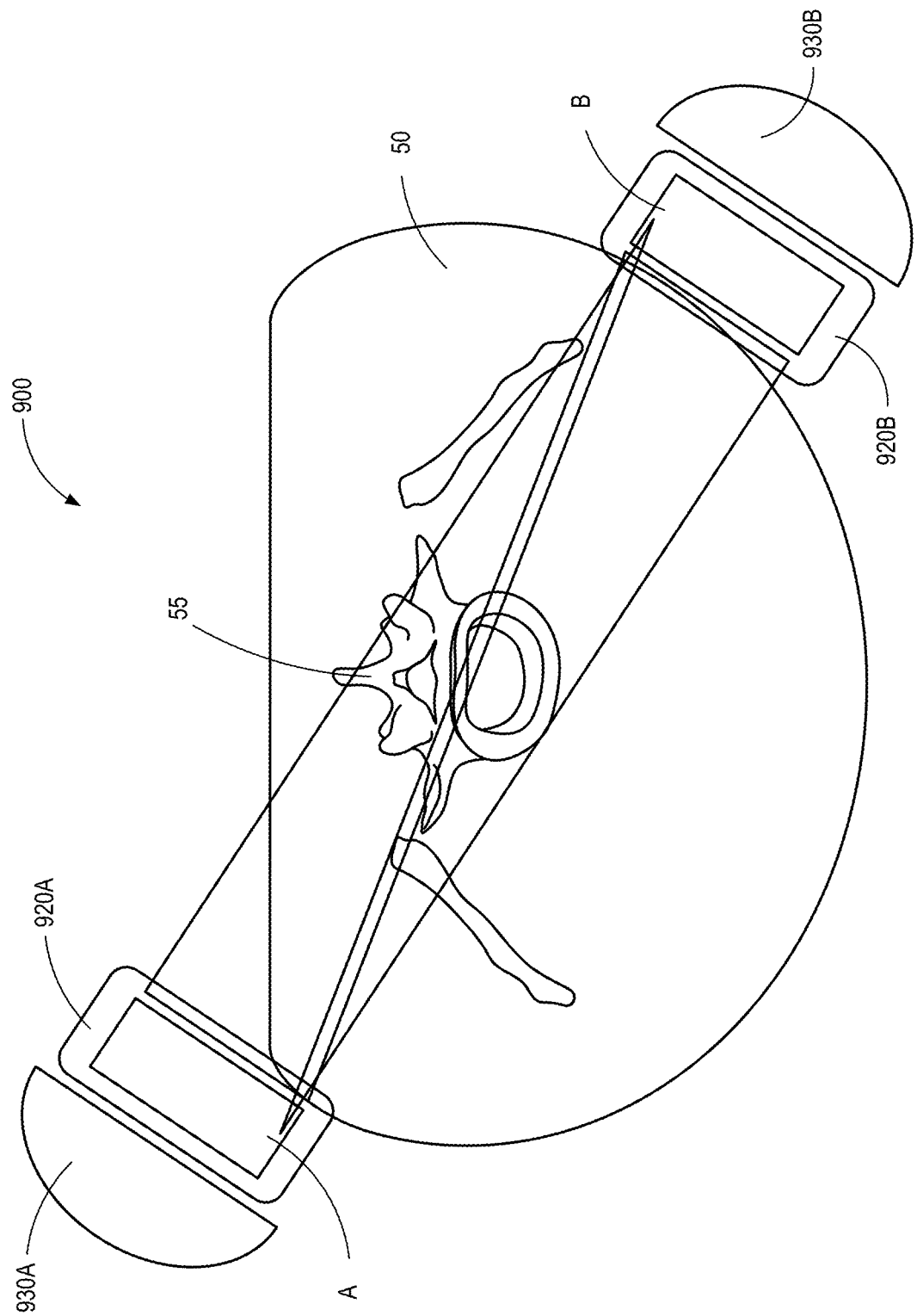
FIG. 9 depicts yet another embodiment of an imaging system.

FIG. 9 illustrates still another embodiment of an imaging system 900. Imaging system 900 comprises paths in which both radiation sources and detectors move together. For example, in some embodiments, the radiation sources and detectors may be coupled together in pairs. For example, a first source A is coupled with a first detector panel 920A and a second source B is coupled with a second detector panel 920B. The first pair comprising source A and detector panel 920A may be coupled with a first track system 930A and the second pair comprising source B and detector panel 920B may be coupled with a second track system 930B. Track 930A may be configured to move source A and detector panel 920A in a path, such as a circular or other curved path, for example, above patient 50. Track 930B may similarly be configured to move source B and detector panel 920B in a second path below patient 50.

FIG. 9 can be representative of two alternative embodiments of imaging system 900. In a first such embodiment, as discussed about, the source(s) may be coupled directly with detector(s) immediately adjacent to one another. In a second such embodiment, the source(s) may be spaced apart from the detector(s) but in the same path (similar to the embodiment depicted in FIG. 4). With respect to the latter of these two possible embodiments, FIG. 9 may represent two overlapping images taken at two different points in time during an imaging process within which sources A and B, and detectors 920A and 920B, are moving.

Of course, those of ordinary skill in the art will appreciate that a wide variety of alternatives are possible. For example, a greater number of source/detector pairs may be used. In some embodiments, two such pairs may be provided in a first path and two such pairs may be provided in a second path separated from the first path. In certain preferred embodiments, the two paths may be positioned such that a patient, or at least a portion of a patient to be imaged, may be positioned in between the two paths. In other embodiments, four source/detector pairs may be provided in the first path and four in the second path. Preferably, each source/detector pair has a corresponding source detector pair in a distinct path that can be considered "linked" in some way. For example, one source/detector pair may be positioned to face a second source/detector pair such that radiation from a source from one such pair will always be detected by a detector from the "linked" source/detector pair. As such, the linked source/detector pairs may be configured to move at at least substantially the same angular speed and may be moved and angled so as to maintain a suitable angling to provide for such a result.

The gantries and track systems disclosed herein may, in some embodiments, be combined such that radiation sources and/or detectors may be moved in a rotating gantry comprising a track configured to move the sources and/or detectors in one or more predefined paths. For example, in some embodiments, a chain powered by a motor may be used to move sources and/or detectors in one or more predefined paths, such as a single circular, oval, or other curved path.

Figure 10:
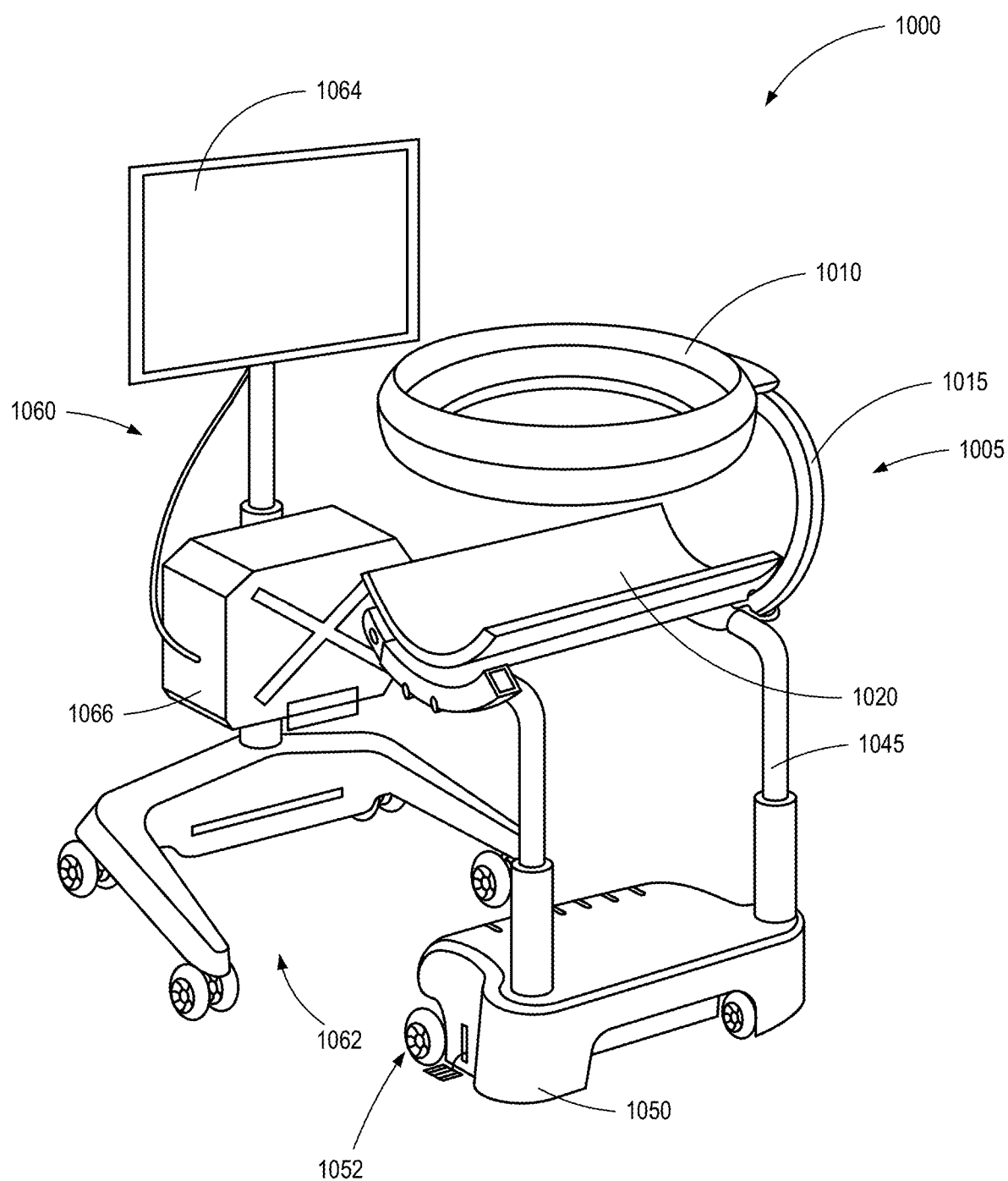
FIG. 10 is a perspective view of an embodiment of an imaging system.

FIG. 10 illustrates another embodiment of an imaging system 1000. Imaging system 1000 comprises an imaging assembly 1005 comprising a gantry 1010 and a detector 1020. Gantry 1010 comprises one or more radiation sources. In some embodiments, gantry 1010 may be configured to move such radiation source(s) in one or more predefined paths. For example, in some embodiments, a track system may be provided, as discussed above. Gantry 1010 may further comprise a generator and/or battery if desired. The battery may be embedded inside the gantry housing to decrease the cabling between static and moving parts of the system. In the configuration depicted in FIG. 10, a surgeon and/or robot can operate and/or manipulate a patient from the center of the "halo" or donut hole of gantry 1010.

System 1000 further comprises a positioning arm 1015 coupled to gantry 1010. Positioning arm 1015 comprises a C-shape that may be configured to hold gantry 1010 and/or a detector, such as detector 1020, rigid with respect to each other. Although other shapes are possible, providing a C shape may allow for rotation of the radiation source(s) and detector(s) together as a single unit, which may be useful to access a patient's anatomy from different angles and/or to capture images from different angles. However, other embodiments are contemplated in which the gantry and/or radiation sources may be positioned/moved (between imaging sessions) independently of the detector(s).

In the depicted embodiment, detector 1020 comprises a curved detector. This detector may therefore be also used as a bed or resting tray such that a patient may, for example, lie down or otherwise rest an anatomical region of interest on the detector panel. In alternative embodiments, however, one or more radiation detectors may be positioned underneath such a bed/tray/panel.

In some embodiments, detector 1020 may comprise a digital flat panel detector configured to capture and digitize x-ray or other electromagnetic radiation absorption images from a conic x-ray projection delivered from one or more radiation sources. The detector(s) and/or detector assembly could alternatively be flat or v-shaped if desired.

System 1000 further comprises a pair of structural raisers 1045 that may be configured to allow imaging assembly 1005 to be moved up and down to accommodate different table heights, patient sizes, etc.

A base 1050 may be provided to, for example, contain power supplies, counterweights, electronics, etc. Wheels 1052 may also be provided to allow for imaging assembly 1005 to be moved about.

In some embodiments, base 1050 may be configured to fit and be stored within a recess of a corresponding workstation comprising, for example, a computer and/or monitor. For example, in the depicted embodiment, a workstation 1060 is provided comprising a recess 1062 for receiving at least a portion of base 1050. Workstation 1060 comprises a monitor 1064 and a computer 1066, which may be used for visualization and image reconstruction.

Figure 11:
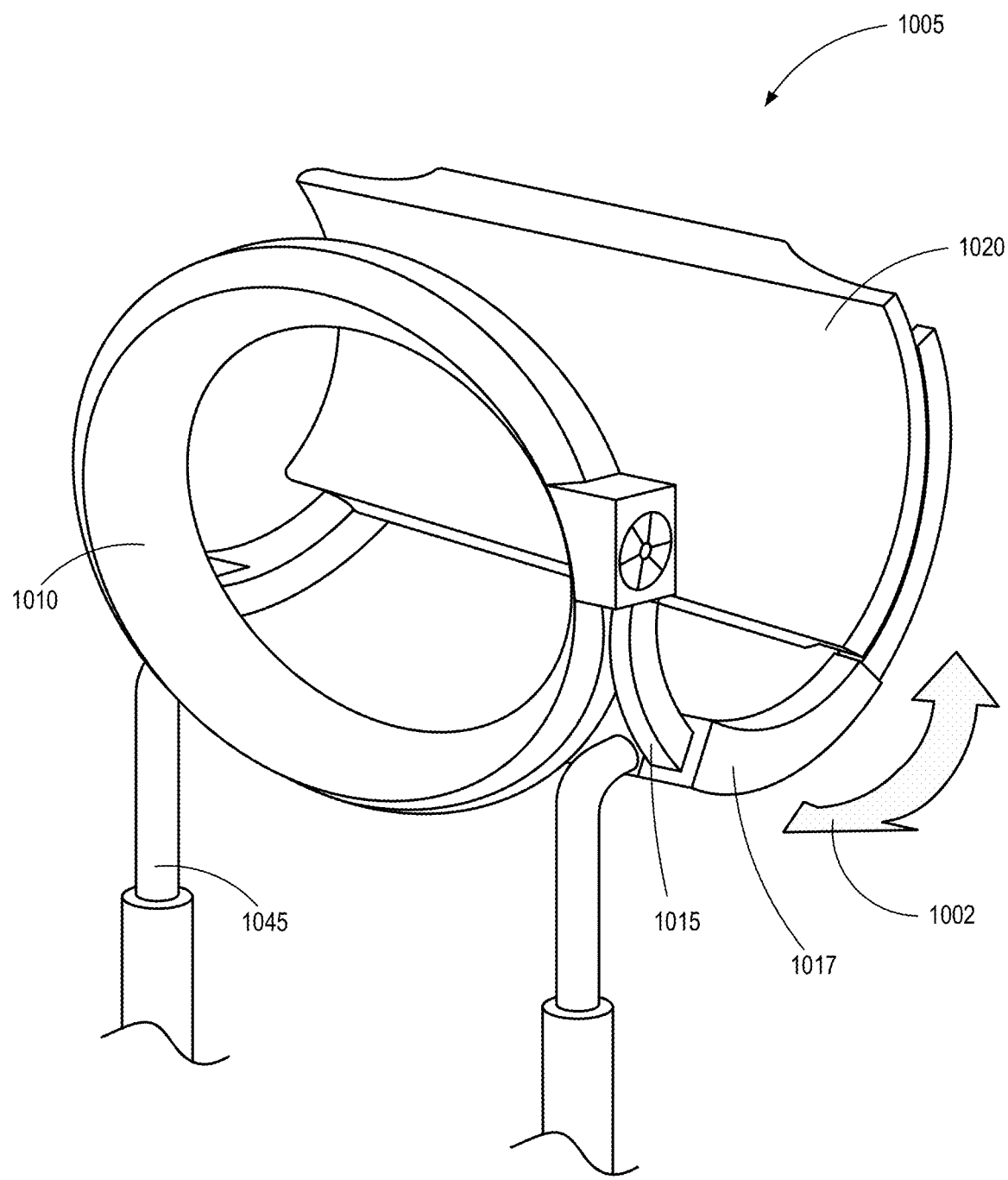
FIG. 11 is a close-up view of the imaging assembly of the imaging system of FIG. 10.

FIG. 11 depicts imaging assembly 1005 of imaging system 1000 in a rotated configuration. One or more portions of imaging assembly 1005 may therefore be configured to allow for rotation to accommodate patient imaging or otherwise make the imaging process more convenient. As shown by arrow 1002, in some embodiments this may be accomplished by inserting positioning arm 1015, which may be coupled to one or both of gantry 1010 and detector 1020, into a corresponding curved housing 1017 in imaging assembly 1005. Detector 1020 may similarly be configured to move along a track defined by housing 1017. One or more of element(s) 1045 may be coupled with one or more housing 1017 elements if desired.

Preferably, gantry 1010 and detector 1020 are movable together as a unit such that the relative positions of the radiation source(s) and detector(s) are preserved. However, alternative embodiments are contemplated in which gantry 1010, or another structure housing or otherwise containing one or more radiation sources, may be positioned/moved in between imaging sessions independently of one or more corresponding radiation detectors.

In one or more of the embodiments described above, the radiation sources may be configured to rotate or otherwise move about a center point of a circular or otherwise curved path and move along the path. In embodiments configured to oscillate about such a path, each source may be configured to move from an initial or first location along the path and then reverse direction at a second location to return to the first location. As the source(s) move, they may be configured to emit radiation at at least two positions along the path. Further, each source can move along a separate open curved path if desired. The open curved paths of the sources can collectively form a circular, elliptical, or other shape. The circular, elliptical, or other shape can be planar or lie partially or entirely out of a single plane.

For example, in some embodiments, in imaging system may comprise four radiation sources and each of the four sources may be configured to move along open curved paths that each have about a 90 degree arc, such that collectively, the four sources have 360 degree coverage (whether the collective path is circular, elliptical, or otherwise).

Figure 12:
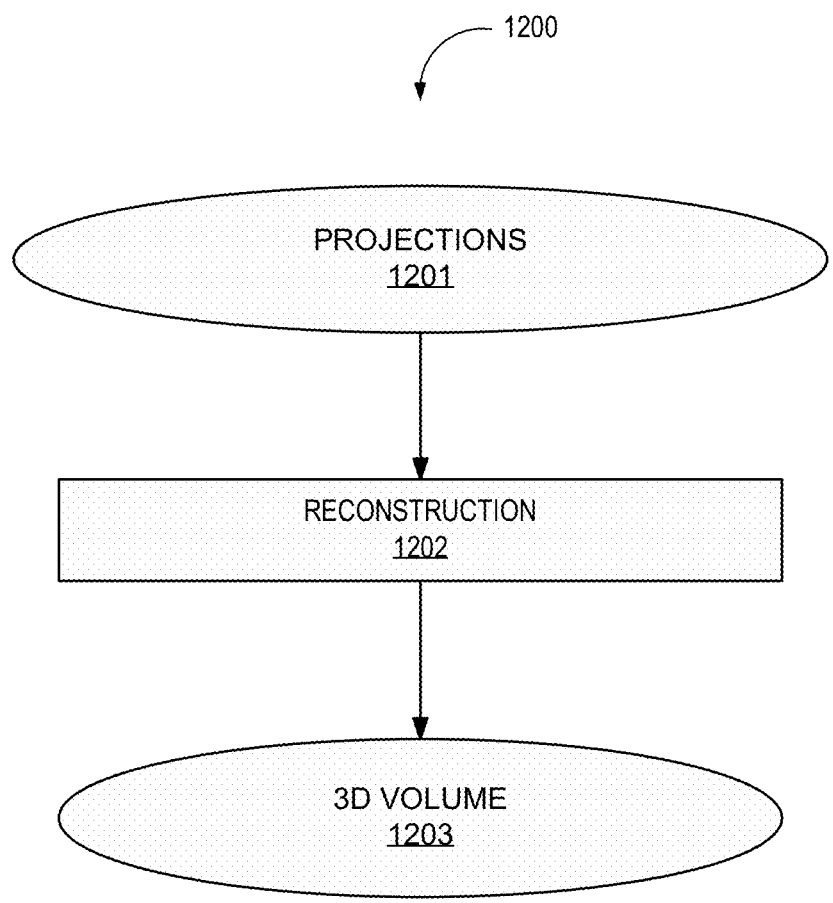
FIG. 12 is a flow chart depicting an implementation of a method for generating reconstruction image data of at least a portion of an object.
Figure 13:
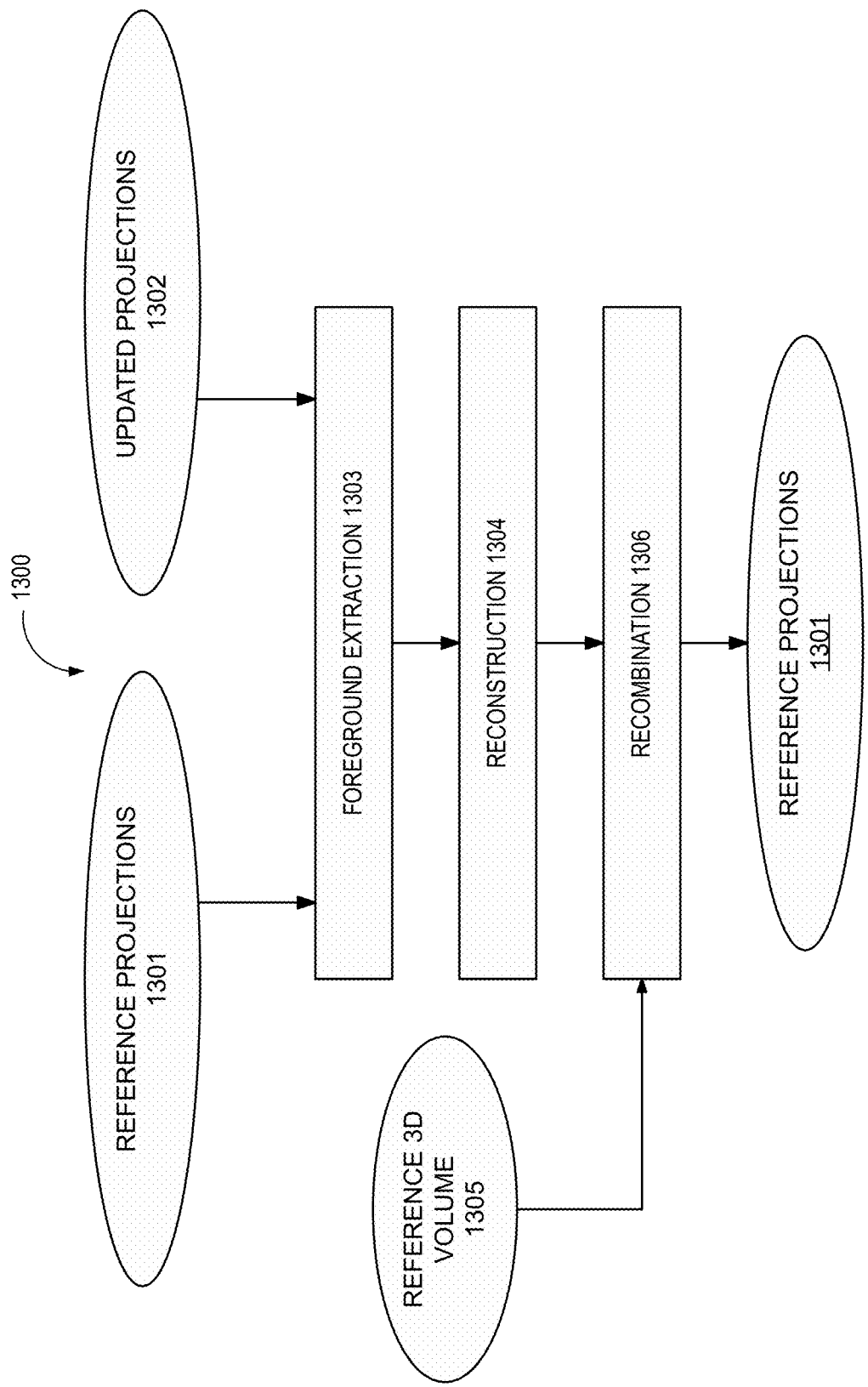
FIG. 13 is a flow chart depicting another implementation of a method for generating reconstruction image data of at least a portion of an object.
Figure 14:
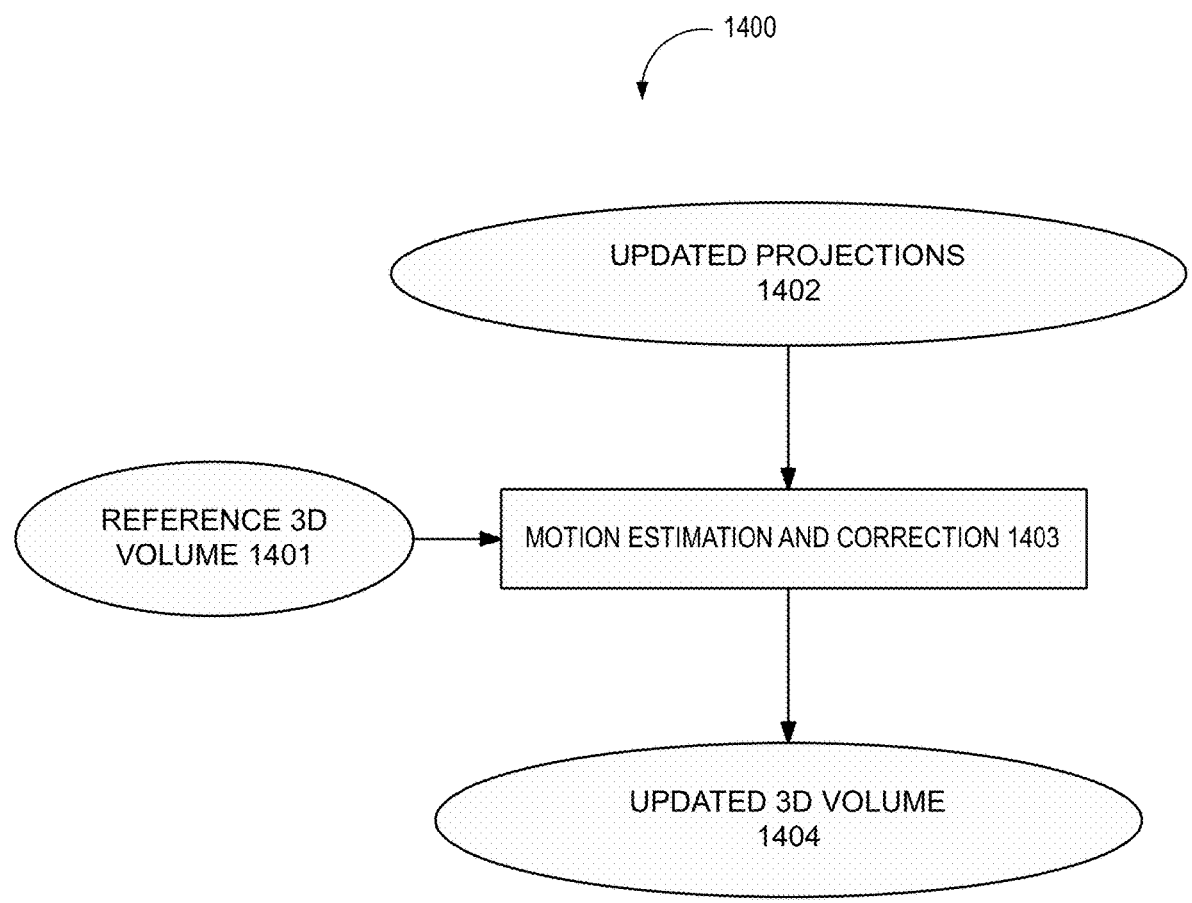
FIG. 14 is a flow chart depicting still another implementation of a method for generating reconstruction image data of at least a portion of an object.

FIGS. 12, 13, and 14 depict, respectively, implementations of imaging methods 1200, 1300, and 1400 that may be performed by one or more of the imaging systems and/or apparatus discussed herein.

In any of the methods disclosed herein, "Projections" may comprise a series of absorption projection images, each associated with the necessary geometric parameters that describe the geometric relationship between the imaged volume and the associated projections.

An example of this methodology is described in Cone-Beam Reprojection Using Projection-Matrices, published in IEEE TRANSACTIONS ON MEDICAL IMAGING, VOL. 22, NO. 10, OCTOBER 2003. This paper is hereby incorporated herein by reference in its entirety.

In these exemplary methods, the output 3D volume may be a volumetric representation that correlates to the volumetric densities of the imaged volume. The output 3D volume can be visualized in different ways that are relevant to the user. A typical visualization method is to show a series of slices of the output 3D volume along certain axis, for example to provide coronal slices, sagittal slices, or axial slices like in Computer Tomography (CT).

In method 1200, a certain number of Projections 1201 may be obtained from an imaging system, for example, the imaging systems and/or apparatus discussed herein. At step 1202, a 3D volume 1203 may be reconstructed from the imaged volume's Projections. For example, an iterative algorithm like an Algebraic Reconstruction Technique (also known as ART, ref. 2) can be used. Examples of such techniques can be found in Algebraic reconstruction techniques (ART) for three-dimensional electron microscopy and x-ray photography, published in Journal of Theoretical Biology 29 (3): 471-81 (December 1970). This paper is also hereby incorporated herein by reference in its entirety.

The quality and speed of the iterative reconstruction depends on the sparsity or density characteristics of the imaged volume. In method 1200, the acquired Projections may be characterized by being dense. In order to obtain a 3D volume with meaningful clinical information, a high number of Projections and/or iterations may be needed, resulting in increased system latency. A solution to achieve faster reconstruction (and thus visualization) based on sparse Projections is described in method 1300, represented in FIG. 13. Similar methods that exploit the sparsity of the data have been proposed, such as in Accurate image reconstruction from few-views and limited-angle data in divergent beam ct, published in J X-Ray Sci. Technology, 14: 119-139 (2006), which is hereby incorporated by reference in its entirety.

In method 1300, at step 1301, a certain number of reference Projections may be obtained.

At step 1302, a certain number of updated Projections may be obtained using an imaging system, for example one of the imaging systems and/or apparatus discussed herein.

At step 1303, a sparse Projection set may be obtained from the reference and updated Projections. This could be possibly implemented using a simple subtraction between reference Projections and updated Projections. The creation of the sparse Projections can be called a foreground extraction.

In some implementations, the reference Projections may be taken from (or be derived from) the physical systems and/or apparatus discussed herein or derived from the reference 3D volume 1305 by, for example, mathematical projection.

Step 1304 may comprise reconstructing the 3D volume of the extracted foreground, and may, in certain implementations, operate in a similar manner as step 1202 in method 1200. Due to the sparsity of the extracted foreground Projections, the reconstruction algorithm requires a lower number of Projections and/or iterations, hence reducing latency.

At step 1306, the 3D volume of the extracted foreground may be recombined with the reference 3D volume 1305 to produce the Updated 3D volume 1307 that can be visualized.

The reference 3D volume in 1305 represents the imaged volume associated with the Projections of 1301. Reference 3D volume may be obtained, for example, using a pre-operative CT-scan, another a-priori image, or the reconstruction of an initial higher resolution tomosynthetic reconstruction.

In some implementations, motion estimation and correction may be used to have a reference 3D volume that best matches reference Projections and/or to ensure sparsity of the foreground extraction. For example, method 1400 may be used to update the reference 3D volume.

Method 1400 may be used for generating an updated 3D volume for visualization or as means to provide a better reference 3D volume in method 1300.

In method 1400, at step 1401, a certain reference 3D volume may be obtained. This reference 3D volume may be obtained, for example, using a pre-operative CT-scan, another a-priori image, or the reconstruction of an initial higher resolution tomosynthetic reconstruction.

At step 1402, a certain number of updated Projections may be obtained using an imaging system, for example, any of the imaging systems and/or apparatus discussed herein.

At step 1403, motion may be estimated and corrected using, for example an iterative gradient descent algorithm, resulting in an updated 3D volume 1404. The motion correction could be, for example, modeled based on 6 degrees of freedom to describe translational and rotational changes.

Methods 1200, 1300, and 1400 may rely on obtaining a certain number of Projections. As such, the system latency in certain implementations may depend on the time it takes to acquire the Projections and the time it takes to execute the reconstruction method and obtain the 3D volume.

Each of the depicted methods 1200, 1300, and 1400 may therefore be used sequentially to provide a sequence of 3D volumes, thereby allowing the user to visualize changes of the imaged volume.

Each of the depicted methods 1200, 1300, and 1400 may also be used in a parallel computational pipeline to provide a faster sequence of 3D volumes. Each reconstruction may be based on a certain number of Projections (for example, 90), with each new execution of the method starting after a fewer number of Projections has been obtained from the system (for example 12, which is smaller than 90). In this case, multiple instances of the method may be run in parallel and the latency may be reduced.

Each of the depicted methods 1200, 1300, and 1400 may be implemented around an iterative algorithm (iterative reconstruction algorithms 1202 or 1304, or iterative motion estimation 1403). Each method can therefore be used continuously by updating the iterative algorithm's input as new input becomes available.

In some implementations, one or more of the depicted methods 1200, 1300, and 1400 may be implemented as a computer program and implemented on highly parallelized architectures, for example on General Purpose Graphical Processing Units (GPGPU).

A computer program implementing any of methods 1200, 1300, and 1400 may use optional multi-resolution techniques to update the volume quickly and refine the image later (start with a low number of updated images, low projective image resolution, low number of voxels and then refine with more images, higher resolution projective images and higher number of reconstructed voxels).

One or more systems disclosed herein may have unique potential to exploit dual/multi energy schemes since radiation sources could be set at different energy levels (kV, or eV). For example, a plurality of radiation sources can be used that have variable or steady energy levels that are generally the same or different from each other.

Some embodiments may also, or alternatively, have a unique potential to exploit digital subtraction schemes since radiation sources can quickly overlap each other and projection images taken from the same position but at different times as the radiation source(s) and/or gantry rotates can be subtracted. Subtracted projection images can feed the 3D algorithm obtaining subtracted 3-D datasets. Subtracting the image projections may improve the quality of the reconstruction since the algorithm attempts to reconstruct a sparser volume.

In some embodiments and implementations, the subtraction can be from projective images taken at different energy levels (kV or eV).

In some embodiments, improved access for surgeons and interventionists may be interchanged with improved access to robots performing the intervention or simplify the integration with other devices (for example with radiotherapy systems that target tumors).

As noted above, the path(s) of the source(s) and/or detector(s) can be used for source(s) and/or detector(s) that are positioned on a first hemisphere of an object. Further, in embodiments in which source(s) and/or detector(s) in a second hemisphere of the object move relative to the object, those source(s) and/or detector(s) in the second hemisphere may also move along any of the variety of paths discussed herein. Additionally, a first path in a first hemisphere may be the same shape as a second path in a second hemisphere, a different shape, translated, rotated, mirror, or otherwise be positioned similarly or dissimilarly relative to the second path, as desired.

The following additional concepts are disclosed herein, which may be useful in performing various implementations of methods and/or creating various embodiments of systems embodying and/or implementing one or more of the inventive concepts below:

Aid to a 3D reconstruction: A 3D model of an imaged object obtained from an optical camera (a 3D optical image reconstruction system) can be used to aid the reconstruction of the imaged object by a 3D x-ray image reconstruction system. For example, when the x-ray imaging system comprises an x-ray CT system, Cone Beam CT system, or a Tomosynthesis system, such as the system disclosed in U.S. patent application Ser. No. 14/198,390 titled "IMAGING SYSTEMS AND RELATED APPARATUS AND METHODS," which application is incorporated herein by reference in its entirety.

Figure 15:
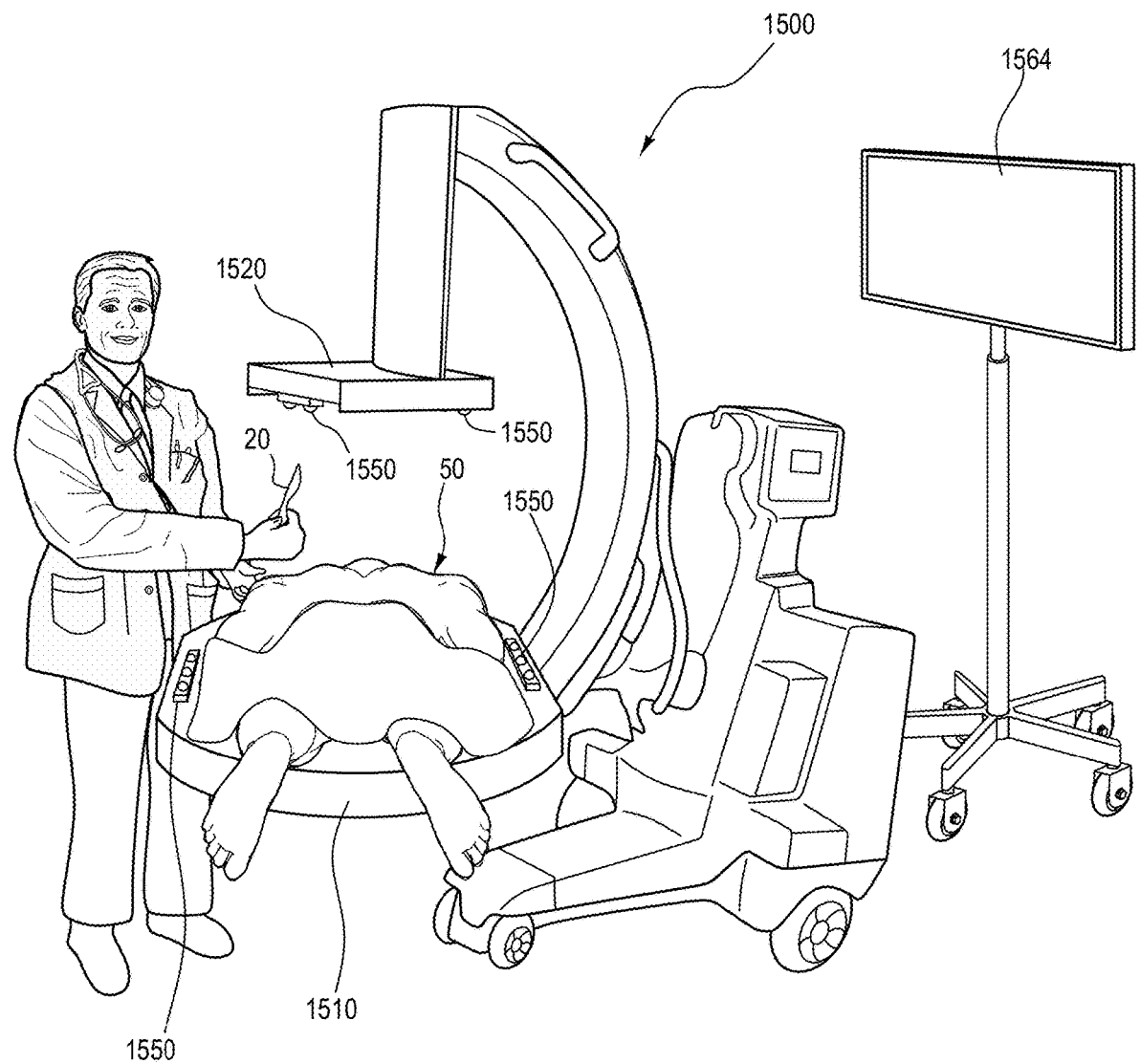
FIG. 15 is a perspective view of an imaging system comprising an x-ray imaging system and an optical imaging system according to some embodiments.

An example of a system for imaging reconstruction using both x-ray tomosynthesis and optical reconstruction is depicted in FIG. 15 at 1500. Imaging system 1500 comprises an x-ray tomosynthesis image reconstruction system comprising a gantry 1510 and a detector 1520. Gantry 1510 comprises one or more (preferably a plurality) of x-ray radiation sources (not shown in FIG. 15). Gantry 1510 may be configured to move such radiation source(s) in one or more predefined paths. For example, in some embodiments, a track system may be provided, as previously described.

As also previously described, imaging system 1500 comprises a detector 1520 positioned on an opposite side of gantry 1510 so that at least part of a patient 50 can be positioned in between gantry 1510 and detector 1520. Gantry 1510 is configured to enclose the plurality of x-ray radiation sources within an enclosed portion of the gantry. Gantry 1510 is further configured so as to avoid having any exposed moving parts during an imaging process using imaging system 1500, and is configured to enclose the plurality of x-ray radiation sources without fully enclosing the patient 50, or any part of patient 50, so as to allow access to patient 50 during the imaging process. Of course, patient 50 may be replaced with another three-dimensional object in alternative embodiments and implementations.

In addition, unlike embodiments described in connection with previous figures, system 1500 further comprises a three-dimensional optical imaging system configured to reconstruct an image of at least a portion of a surface of a target object, such as patient 50, by generating surface three-dimensional image data. The three-dimensional optical imaging system is preferably registered to the x-ray tomosynthesis image reconstruction system so that data from both systems can be used to improve image reconstruction. The three-dimensional optical imaging system comprises one or more optical cameras configured to generate distance/depth data for a surface of a three-dimensional object, such as RGB-D cameras 1550. The depicted embodiment comprises four such optical, depth detecting cameras 1550, two of which are coupled to the detector 1520 and two of which are coupled to the gantry 1510. However, after having received the benefit of this disclosure, those of ordinary skill in the art will appreciate that alternative types of optical cameras, numbers of optical cameras, and placement of optical cameras may be provided.

Cameras 1550 may be configured to reconstruct an outline of a surface of patient 50, or at least a portion of a surface of patient 50, and may be used to generate one or more density constraint profiles to improve the reconstruction of a three-dimensional image of a target region of patient 50 or another three-dimensional object. In preferred embodiments, the three-dimensional optical imaging system is registered to the x-ray tomosynthesis image reconstruction system. For example, the outline or patient surface can be referenced to the same reference frame as the tomographic reconstruction.

In some embodiments and implementations, multiple separate objects may be imaged using the three-dimensional optical imaging system. Thus, for example, a surgical tool 20 and/or an implant, or a combination of tools/implants, may be surface/depth imaged using the three-dimensional optical imaging system. In the example of FIG. 15, the cameras 1550 are rigidly attached to the system 1500 and therefore may be registered to the x-ray tomosynthesis image reconstruction system via a calibration step. The registration can be described or decomposed as a translation 3D vector and three rotations for each camera. In some embodiments and implementations, multiple cameras can jointly provide the patient, tool, and/or implant outline, or parts of it. However, alternative embodiments and implementations are contemplated in which the camera(s) need not be rigidly attached to a component of the system, as explained below.

As also shown in FIG. 15, system 1500 may further comprise a monitor or another suitable display 1564, for reproducing, in some embodiments and implementations in real or near real time, the reconstructed image.

One or more such systems, such as system 1500, may perform a volumetric mass and/or linear attenuation reconstruction. If such systems use an iterative reconstruction algorithm or equivalent, the algorithm can be constrained with the 3D model obtained from one or more optical cameras. Such constraint could be as simple as describing the surface of the object.

Other less simple density constraints could be used as well. The outside of the object can be modeled with a low density (typically air) and this volumetric density constraint may improve the reconstruction, for example, by reducing artifacts related to otherwise incomplete/less complete data for reconstruction. Incomplete data can be limited angle data for reconstruction or limited view of a region of interest reconstruction. Moreover, the inside of the object can be modeled as a continuous function that ties the density outside of the object with the mass and/or linear attenuation from the solving model, for example from the 3D model in an iterative reconstruction algorithm.

Aid to a 4D reconstruction with a tracking system I: Some embodiments of the invention may allow for accounting for motion of an imaged object (or objects) to improve its (their) volumetric mass and/or linear attenuation reconstruction (for example, with a reconstruction based on x-rays). A method to reconstruct 4D scenes may rely on an evolution model that is updated from time to time. The initial reconstruction and the updated reconstructions may be distinguished as a typical case, but this could be imagined in more general terms. Positional changes can happen and be captured by a tracking system any time from the initial reconstruction to the last reconstruction (including any time in between). These changes may include patient/table motion, gantry displacements, and/or surgical tools that are the object of the mass attenuation reconstruction at least partially in the field of view, separately or jointly reconstructed and tracked. In this context, tracking systems can be, for example, optical tracking systems (such as surgical navigation tracking systems), optical 3D reconstruction systems, or electromagnetic tracking systems to name a few.

Some systems may implement an algorithm that uses x-ray imaging to observe motions and evolves the 4D mass attenuation reconstruction based on such observed motion. Such observations may be further improved if they were replaced (or combined, see next section) with motions observed from the other tracking system. Therefore, some embodiments and/or implementations of the invention may deal with accounting for motion that can be captured externally to the mass attenuation reconstruction system by means of tracking, for example via video monitoring of the scene. Extracted motion parameters can be transferred to the mass attenuation reconstruction engine.

Figure 16:
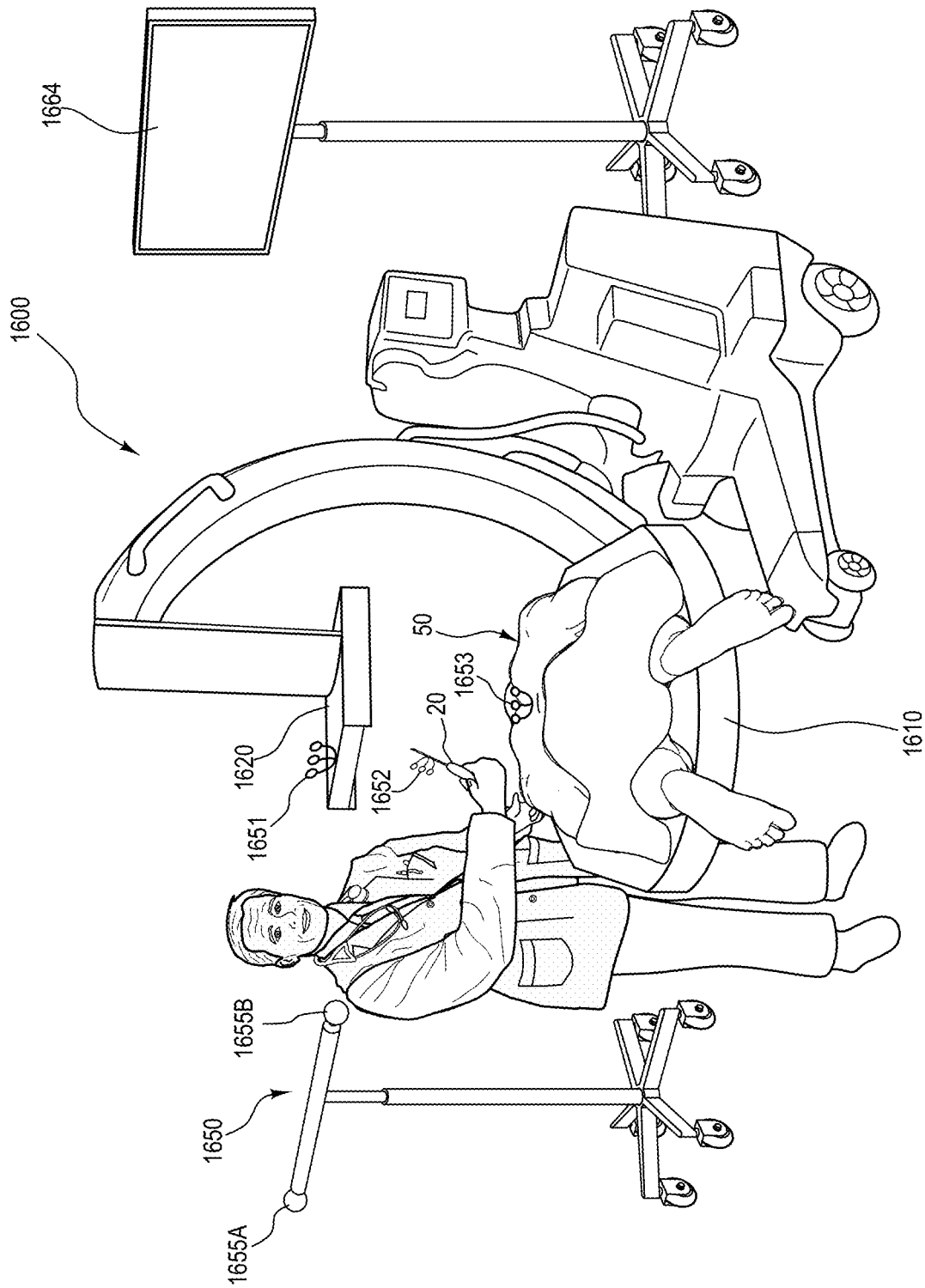
FIG. 16 is a perspective view of an imaging system comprising an x-ray imaging system and a tracking system according to some embodiments.

Thus, another example of an imaging system is depicted in FIG. 16 at 1600. System 1600, like system 1500, system 1600 comprises an x-ray tomographic system comprising a detector 1620 positioned on an opposite side of a gantry 1610 so that at least part of a patient 50 can be positioned in between gantry 1610 and detector 1620. Gantry 1610 is, again, configured to enclose a plurality of x-ray radiation sources within an enclosed portion of the gantry. Gantry 1610 is further configured so as to avoid having any exposed moving parts during an imaging process using imaging system 1600, and is configured to enclose the plurality of x-ray radiation sources without fully enclosing the patient 50, or any part of patient 50, so as to allow access to patient 50 during the imaging process.

In addition, system 1600 further comprises a three-dimensional motion tracking system 1650 comprising one or more tracking cameras 1655, such as infrared tracking cameras, and one or more markers, such as fiducials. In the depicted embodiment, three-dimensional motion tracking system 1650 comprises two infrared tracking cameras 1655A and 1655B, both of which are mounted on a movable stand or assembly. In addition, three markers are used to track fiducial markers that reflect infrared light, namely, a first marker 1651 positioned on a part of the x-ray tomographic system, such as on detector 1620, a second marker 1652 positioned on a surgical tool 20, and a third marker 1653 positioned on a desired portion of patient 50, such as within a region of interest of patient 50.

The three-dimensional motion tracking system 1650 is configured to provide motion information, such as, for example, motion absolute to the tracking cameras 1655A and/or 1655B or a fixed portion of the related stand/assembly, and/or motion relative between each tracked object. Such motion information can be used to improve a 4D reconstruction, particularly if the reconstruction is a model-based reconstruction including motion.

In some embodiments, the combined system 1600 may also be configured to provide information to identify a particular surgical tool 20 that is in the region of interest (and thus which radiodensity is expected) and/or where the tool 20 is located (and thus which radiodensity is expected in specific areas of the reconstructed image). In some embodiments and implementations, such information may be used improve the reconstruction by adding this information as a constraint to an iterative reconstruction algorithm. As previously mentioned, the tracker/cameras are shown mounted to a movable pole in the embodiment of FIG. 16, and are therefore not rigidly attached to the x-ray tomographic system. Thus, a registration between the x-ray tomographic system, the three-dimensional motion tracking system 1650, and the surgical tool(s) 20 may be performed. Because this process would be simpler (and constant) if the camera(s) were instead fixed to the x-ray tomographic system, alternative embodiments are contemplated in which the three-dimensional motion tracking system 1650 may not be movable relative to the x-ray tomographic system.

As shown in FIG. 16, system 1600 may further comprise a monitor or another suitable display 1664, for reproducing, in some embodiments and implementations in real or near real time, a reconstructed image.

Figure 17:
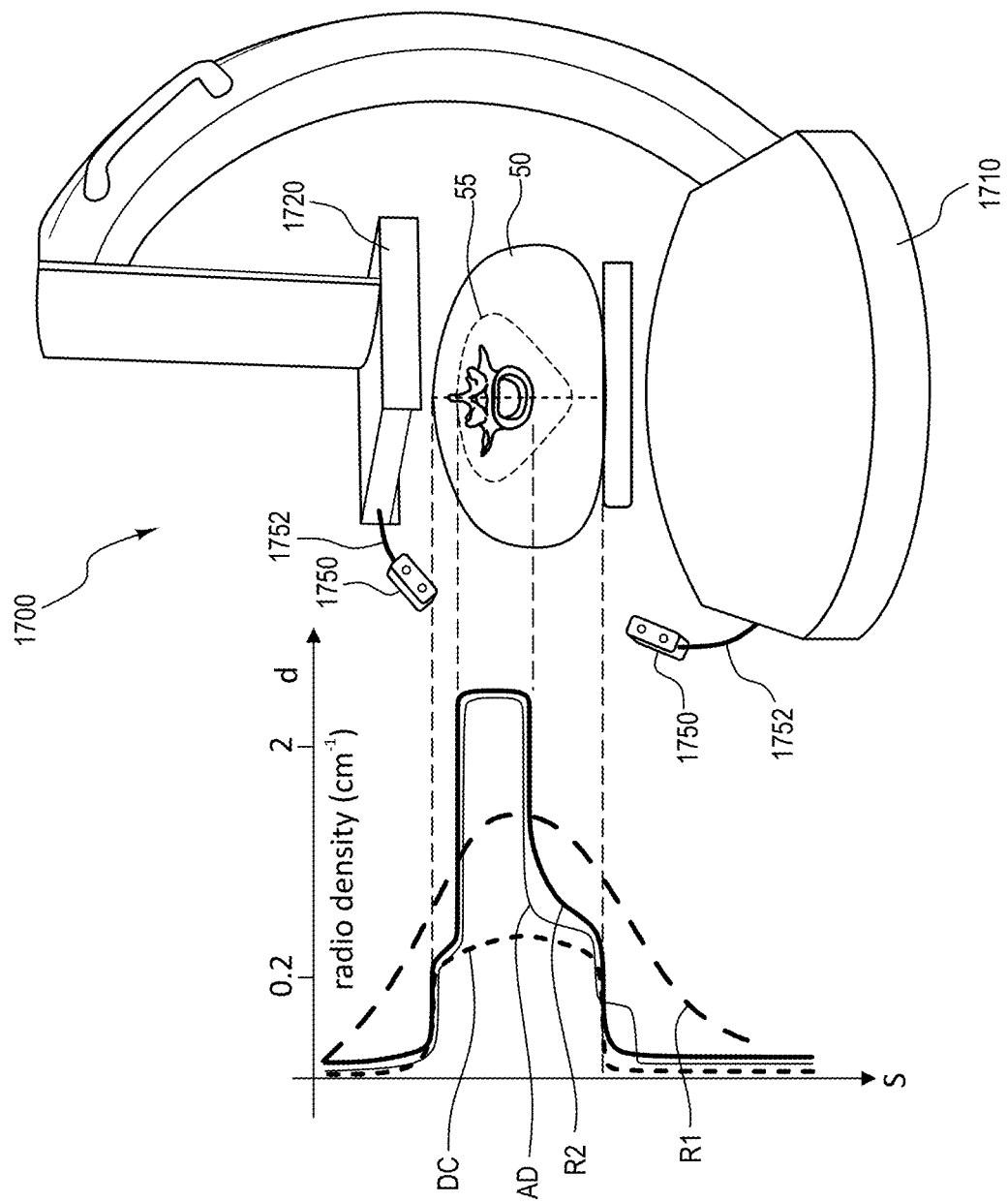
FIG. 17 depicts an imaging system comprising an x-ray imaging system and an optical imaging system with a graph illustrating how using the inventive principles of the imaging system may allow for improving the accuracy of a density profile associated with a region of interest of a patient.

Yet another example of an imaging system 1700 is depicted in FIG. 17. As shown in this image, system 1700 again comprises an x-ray tomographic system comprising a detector 1720 positioned on an opposite side of a gantry 1710 so that at least part of a patient 50 can be positioned in between gantry 1710 and detector 1720. Gantry 1710 is, again, configured to enclose one or more (preferably a plurality) of x-ray radiation sources within an enclosed portion of the gantry 1710. Gantry 1710 is further configured so as to avoid having any exposed moving parts during an imaging process using imaging system 1700, and is configured to enclose the plurality of x-ray radiation sources without fully enclosing the patient 50, or any part of patient 50, so as to allow access to patient 50 during the imaging process.

System 1700 further comprises a three-dimensional optical imaging system configured to reconstruct an image of at least a portion of a surface of a target object, such as patient 50, by generating surface three-dimensional image data. The three-dimensional optical imaging system is preferably registered to the x-ray tomosynthesis image reconstruction system so that data from both systems can be used to improve image reconstruction. The three-dimensional optical imaging system comprises one or more optical cameras configured to generate distance/depth data for a surface of a three-dimensional object, such as RGB-D cameras 1750. The depicted embodiment comprises two such optical cameras 1750, one of which is coupled to the detector 1720 and one of which is coupled to the gantry 1710. In the depicted embodiment, cameras 1750 are mounted to their respective components of the x-ray tomographic system using mounting posts 1752. However, again, alternative types of optical cameras, numbers of optical cameras, and placement of optical cameras may be provided as desired.

Cameras 1750 may be configured to reconstruct an outline of a surface of patient 50, or at least a portion of a surface of patient 50, and may be used to generate one or more density constraint profiles to improve the reconstruction of a three-dimensional image of a target region of patient 50 or another three-dimensional object. In preferred embodiments, the three-dimensional optical imaging system is registered to the x-ray tomosynthesis image reconstruction system. For example, the outline or patient surface can be referenced to the same reference frame as the tomographic reconstruction. This information from both systems can be combined to improve image resolution.

More particularly, as illustrated in the density profiles in the chart included in FIG. 17 (density profiles are shown in one dimension for simplicity), using a density constraint allows the reconstruction algorithm to find a solution that is closer to the actual density of the region of interest 55 of patient 50. Thus, by using a three-dimensional optical imaging system to apply a density constraint to the surface of patient 50, as shown in line DC in FIG. 17, a reconstructed density using this density constraint (shown at line R1) may be improved upon by using the density constraint, as shown at line R2), which is much closer to the actual density profile (shown at line AD) of the patient 50 and the region of interest 55.

Figure 18A:
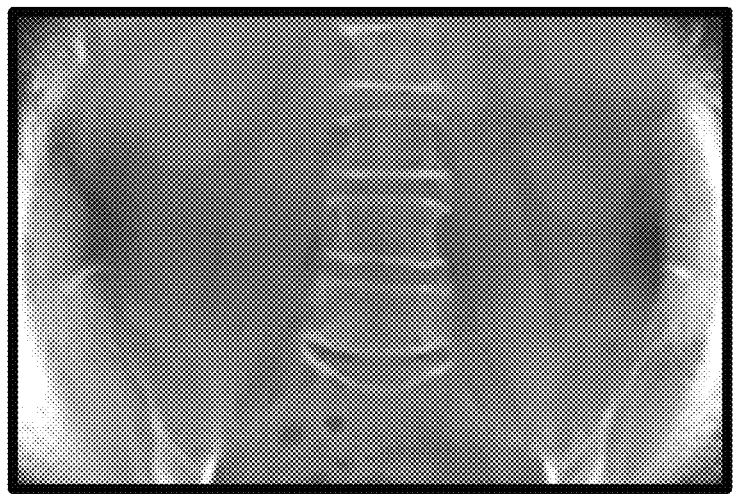
FIGS. 18A and 18B depict, respectively, an unconstrained reconstruction and a constrained reconstruction of a spine anatomy.
Figure 18B:
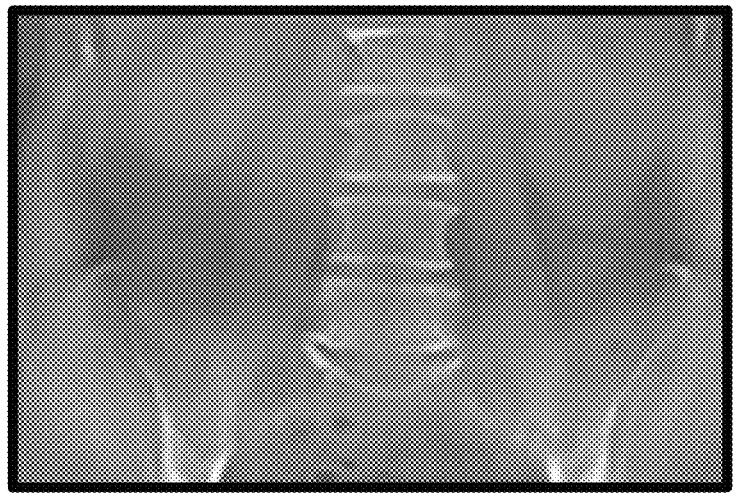

Thus, having RGB-D cameras 1750, or other suitable elements of an optical imaging system, provide an outline of the patient 50 that can be used to constrain the solution in an iterative reconstruction algorithm, higher resolution may be provided. In other words, the density matches more closely the actual density. FIGS. 18A and 18B depict, respectively, reconstructions of a particular anatomical region of interest, and extending beyond the region of interest, without and with use of this density constraint methodology. In the case of the constrained reconstruction (FIG. 18B), the density beyond the surface of the patient is constrained to zero in an iterative reconstruction scheme. The quality of the tomosynthesis reconstruction is improved, and the reduction of truncation artifacts is noticeable by comparing these images.

Figure 19:
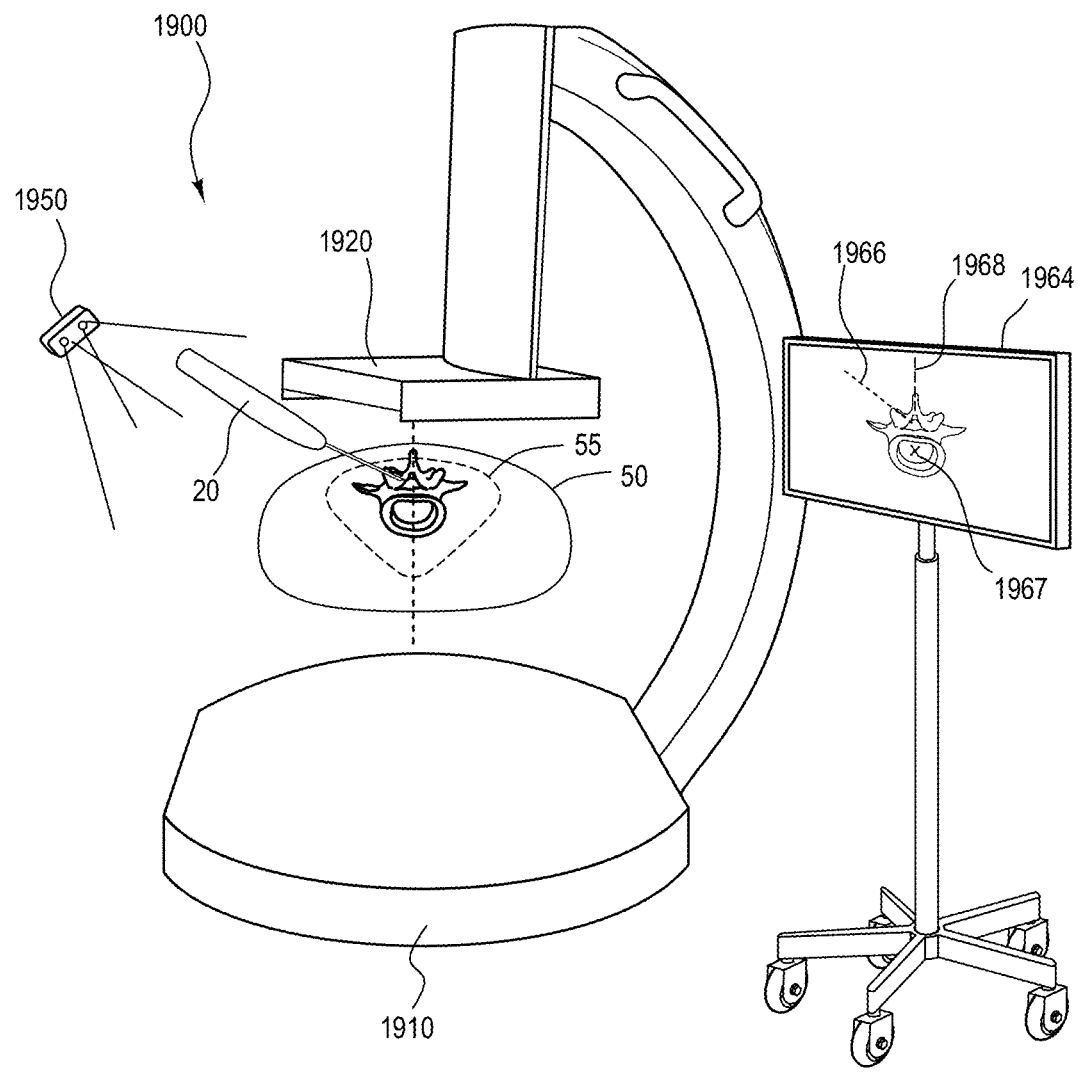
FIG. 19 is a perspective view of an imaging system comprising an x-ray imaging system and an optical tracking system for tracking and imaging a surgical tool along with a region of interest according to some embodiments.

FIG. 19 depicts still another example of an imaging system 1900. Imaging system 1900 again comprises an x-ray tomosynthesis image reconstruction system comprising a gantry 1910 and a detector 1920. As previously mentioned, gantry 1910 comprises one or more (in some embodiments, a plurality) of x-ray radiation sources and may be configured to move such radiation source(s) in one or more predefined paths, such as along a circular path adjacent to a perimeter of gantry 1910, for example.

As also previously described, imaging system 1900 also comprises a three-dimensional optical imaging system configured to reconstruct an image of at least a portion of a surface of a target object, such as patient 50, by generating surface three-dimensional image data. The three-dimensional optical imaging system is preferably registered to the x-ray tomosynthesis image reconstruction system so that data from both systems can be used to improve image reconstruction. The three-dimensional optical imaging system of imaging system 1900 comprises one or more optical cameras 1950, such as an RGB-D camera, configured to generate distance/depth data for a surface of a three-dimensional object, such as a region of interest 55 of a patient 50.

The depicted embodiment comprises a single such optical camera 1950. However, as previously mentioned, other numbers and/or types of cameras may be used. Camera 1950 may be physically decoupled from the x-ray tomosynthesis image reconstruction system, as depicted in FIG. 19. Thus, for example, camera 1950 may be mounted to a stand, table, or other external component of the system.

Camera 1950 may be used to observe and/or track various items, such as a surgical tool 20 and/or patient 50. Because camera 1950 is preferably registered to a three-dimensional image being reconstructed by the x-ray tomosynthesis image reconstruction system, a current trajectory 1966 of the surgical tool 20 can be generated and, in some embodiments and implementations, may be reproduced on a display 1964 in the reconstructed region of interest 55 along with one or more elements/features in the reconstructed region of interest 55. In some such embodiments and implementations, system 1900 may be configured to generate and/or display trajectory 1966 before tool 20 has entered region of interest 55 based upon its tracked movement outside of patient 50. This may be useful for intra-operative planning. For example, this feature may allow a surgeon/technician to select a desired skin entry point and "navigate" to a target point, allowing the surgeon to adjust during the tool insertion.

In some such embodiments and implementations, system 1900 may be configured to generate and/or display other elements used to assist a surgeon/technician during a procedure. For example, as also shown in FIG. 19, a user may be allowed to input a target 1967 and this target may be displayed along with the reconstructed image on display/monitor 1964. By comparing target 1967 with the current trajectory 1966 of tool 20, system 1900 may be configured to allow a surgeon/technician or other user to select a preferred trajectory for the surgical instrument relative to the region of interest and/or dynamically calculate a variance metric between the preferred trajectory and the current trajectory 1966. This may allow, for example, system 1900 to create and/or display a correctional trajectory 1968 to target 1967 so that a user can adjust movement of tool 20 in real time, or near real time, during surgery.

In some embodiments and implementations, system 1900 may be configured such that the display 1934 displays other information, such as a number corresponding with the variance metric, in addition to or as an alternative to the image in FIG. 19 illustrating both the trajectory 1966 and the preferred trajectory 1968. In some embodiments and implementations, system 1900 may be configured such that a user can select a target within the region of interest of a target object, such as target 1967, and system 1900 may also display a current distance between the tool 20 and the target 1967.

In some embodiments and implementations, system 1900 may be configured to dynamically adjust the region of interest 55 in response to movement of the tool 20. For example, in some such embodiments and implementations, system 1900 may be configured to dynamically define the region of interest 55 so as to contain a point adjacent to a distal tip of the tool 20, such as dynamically modifying display 1964 as the region of interest 55 is defined by movement of the distal tip of the tool 20.

Figure 20:
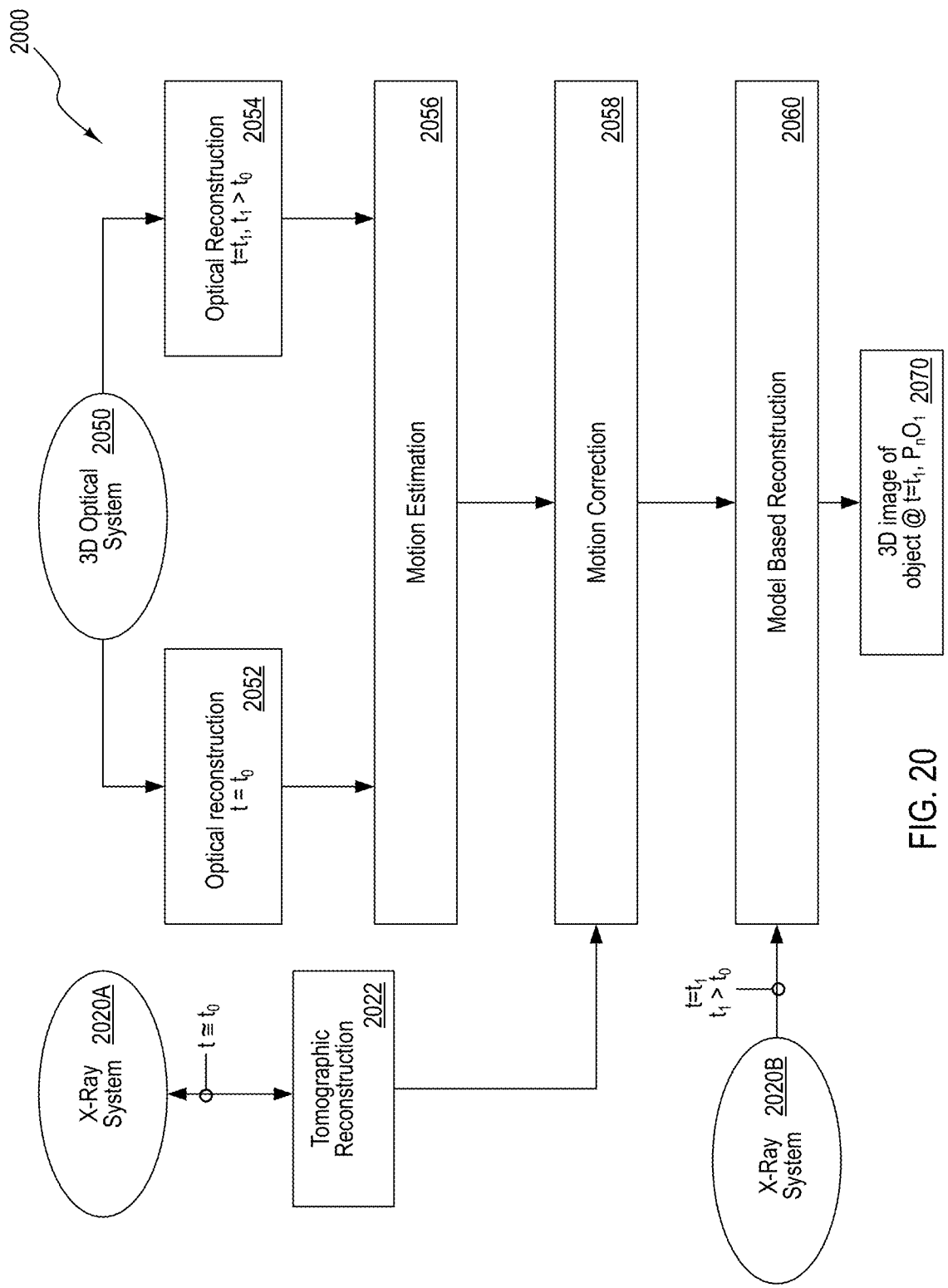
FIG. 20 is a schematic diagram illustrating the operation of an imaging system comprising a 3D optical system and an x-ray system according to some embodiments and implementations.

FIG. 20 depicts a schematic representation of still another example of an imaging system 2000. As depicted in this figure, a 3D optical system 2050, which may comprise an infrared tracking system or, in other embodiments, another suitable tracking system, may be combined with one or more x-ray systems 2020 to provide a 4D reconstruction. In some embodiments and implementations, the 4D reconstruction may comprise a model-based reconstruction. In the depicted embodiments, two x-ray systems 2020A and 2020B are depicted, although those of ordinary skill in the art will appreciate that the same optical system may be used to perform the steps of systems 2020A and 2020B.

As depicted in FIG. 20, the optical tracking system 2050 may provide a first 3D surface reconstruction at $t=t_0$ when the imaged object is in an initial Position and Orientation (PnO) PnO_0 at 2052. The optical tracking system 2050 may then provide a second 3D surface reconstruction at $t=t_1$ when the imaged object is in Position and Orientation (PnO) PnO_1 at 2054, which differs from PnO_0.

The motion between PnO_0 and PnO_1 may then be estimated at 2056. For example, in some embodiments and implementations, the motion of the 3D surface may be assumed to be rigid, or at least substantially rigid, and the motion may be identified that minimizes the difference between the two surfaces (i.e., PnO_1-0). This may represent the translation and series of rotations that explain the motion of the 3D surface. In embodiments and implementations utilizing a tracking system, however, there may no need to infer the motion from the surface. Instead, the system may directly provide the motion from, for example, reflective fiducial markers, such as markers 1651-1653 in system 1600.

One or more x-ray systems, such as x-ray system 2020A, may also provide x-ray projections of the imaged object, or at least a portion of the imaged object, preferably at or at least substantially at $t=t_0$, as indicated at step 2022. Preferably, the x-ray system 2020A is used to reconstruct a 3D image of the object via tomographic reconstruction. In even more preferred embodiments and implementations, the x-ray system 2020A provides tomosynthesis reconstruction of at least a portion of the imaged object. The 3D image may represent the object at to in PnO_0.

Motion correction may then be applied to the reconstructions from both the optical system 2050 and the x-ray system 2020A at 2058. For example, in some embodiments and implementations, a 3D to 2D image registration algorithm may be used based on the projection(s) of the 3D image by minimizing the difference with the actual measured projections.

The 3D image may be updated by applying translation and/or rotation ("virtually moving") from the optical system 2050 using the motion estimation PnO_1-0. This image may represent the object at $t=t_0$ in position PnO_1.

X-ray system 2020 $b$ (or x-ray system 2020A) may then provide projections of the imaged object (or a portion of the imaged object) at a time at or at least substantially equal to time $t_1$ (while the object is in PnO_1). The projection at or at least substantially at $t=t_1$, together with the virtually-moved 3D image, may be used in a model-based reconstruction, as discussed above, at step 2060 to provide a 3D image of the object at $t=t_1$, in PnO_1 at 2070.

In some embodiments and implementations, the newly used projections can be used to model discrepancies between the observed projections and the projections of the virtually moved object. For example, if a surgical tool was added between $t_1$ and to, system 2000 may be able to reconstruct the surgical tool by subtracting the newly acquired projections with virtual projections from the virtually moved model, as explained above.

Other aspects of various embodiments and/or implementations in the motion compensation area may involve combining, or blending (for example, by averaging or otherwise taking into account) or by using detected motion as a seed for an optimization engine that attempts to observe such motion for later use in a 4D mass attenuation reconstruction. In embodiments using a 3D optical reconstruction system, such as system 2000, motion can be estimated based on patient surface displacements.

As previously mentioned, model-based or layered-based 4D reconstruction may utilize tracking systems, such as 3D tracking systems in some embodiments. A mass density 4D reconstruction system may model the scene by assuming that the imaged object is a composition of domains, for example, objects or layers, that may themselves be modeled and/or reconstructed individually and then can be recombined into a global 4D reconstructed scene. Each domain model or reconstruction may benefit via one or more of the mechanisms described above. One such technical mechanism can be the identification of domain projection matrices from the tracking system, when the tracking system is capable to track the domains individually. For example, an optical tracking system can track multiple surgical tools and the patient by having individual optical references, and an optical 3D reconstruction system can track multiple objects via segmentation and modeling based on rigid object/color and motion.

Figure 21:
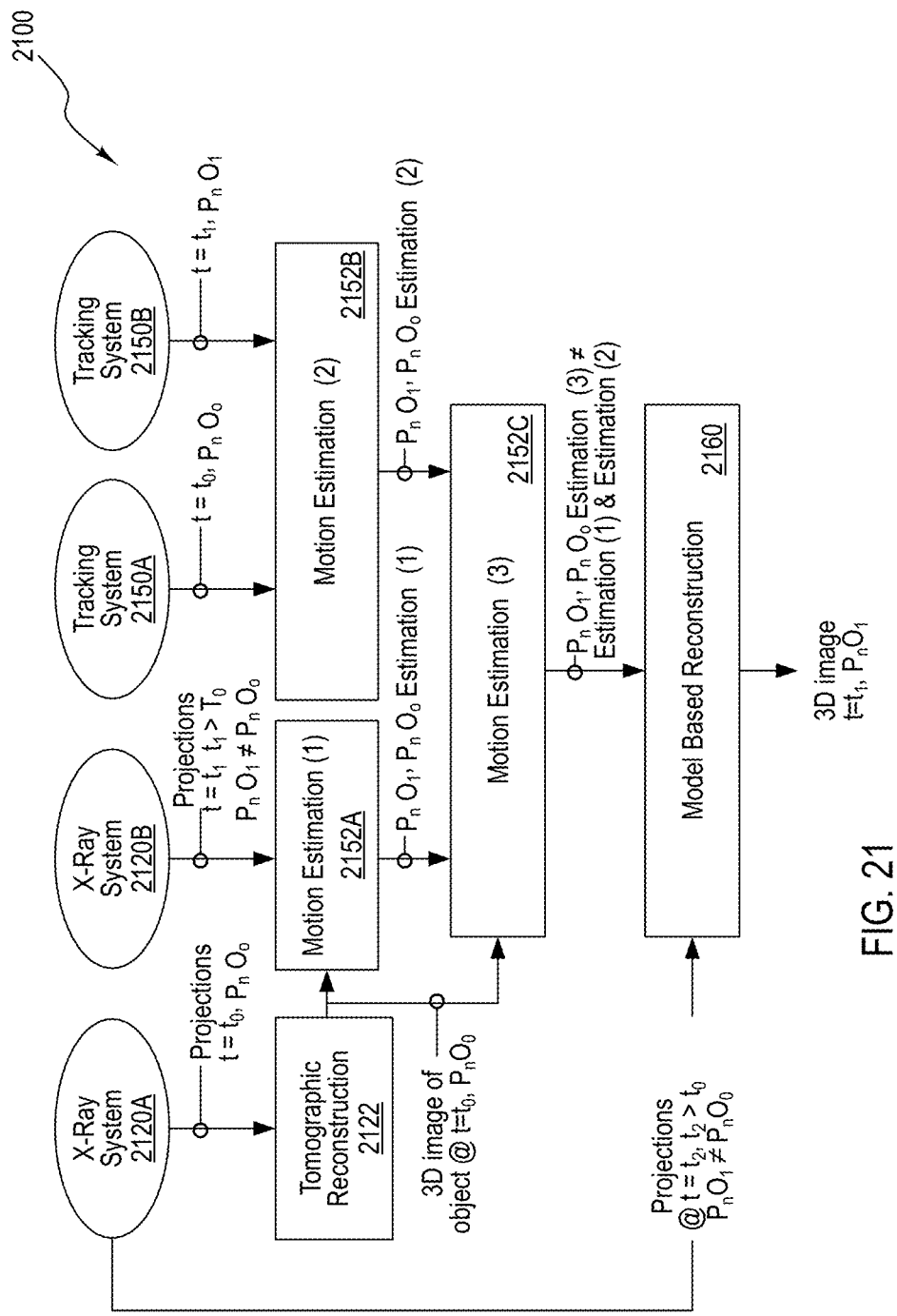
FIG. 21 is a schematic diagram illustrating the operation of an imaging system comprising a tracking system and an x-ray system according to some embodiments and implementations.

A more specific example of such a system is shown in FIG. 21 at 2100. System 2100 may comprise one or more x-ray systems, such as x-ray tomosynthesis image reconstruction systems, and one or more tracking systems, such as 3D tracking systems. Although two x-ray systems 2120A and 2120B and two tracking systems 2150A and 2150B are depicted in FIG. 21, it should be understood that a single x-ray system and a single tracking system may be used instead.

In some embodiments and implementations, system 2100 may be configured to use motion estimations from both the x-ray system(s) 2120A/2120B and the tracking system(s) 2150A/2150B by combining motion estimations from both modalities.

The x-ray system(s) 2120A/2120B may provide projections of an imaged object (in PnO_0) at, or at least substantially at, $t=t_0$. The projections may then be used to tomographically reconstruct the object and provide a 3D image of the object ($t=t_0$, PnO_0), as indicated at step 2122.

Tracking system(s) 2150A/2150B may be used to observe the position of the imaged object (in PnO_0) at $t=t_0$.

Updated x-ray projections of the object from x-ray system(s) 2120A/2120B at substantially $t=t_1$ may be used to infer the motion of the object between to and $t_1$, for example, by finding the motion that minimizes the difference between the new projection and virtual projections of the first image. This first motion estimation is indicated at step 2152A.

Tracking system(s) 2150A/2150B may be used to observe the position of the object at $t=t_1$, and infer the motion of the object between to and $t_1$ and provide a second motion estimation at step 2152B The first and second motion estimations from steps 2152A and 2152B may then be used in combination to obtain a third, more accurate, motion estimation at 2152C. In some embodiments and implementations, this may be performed using a weighted average. Alternatively, the second motion estimation may be used as a seed to the first motion estimation, which may speed up the first motion estimation.

The projection at $t=t_1$, together with the initial 3D image and the motion estimation, may be used to provide a 3D reconstruction 2160 of the object at $t=t_1$, in PnO_1. For example, the initial 3D image can be first virtually moved given the estimated motion and, together with the newly acquired projections, can be used in a model based reconstruction, as previously mentioned. This image is more accurate than the initial reconstruction 2122 because the newly-acquired projections can be used to model discrepancies between the observed projections and the projections of the virtually moved object. For example, if a surgical tool was added between $t_1$ and $t_0$, the system may be configured to reconstruct the surgical tool by subtracting the newly acquired projections with virtual projections from the virtually moved model, as explained above.

As previously mentioned, in some embodiments and implementations, a trajectory of a surgical tool, implant, and/or other movable object relative to a region of interest may be visualized in a mass density reconstruction. For example, a mass density 3D reconstruction may be registered with a 3D optical image reconstruction system to allow for performing intraoperative planning when the instrument/implant is still outside of the x-ray reconstructed volume (the patient's body, for example).

In its simplest form, this may be achieved by visualizing the extended trajectory of the instrument/implant that is still outside the body, entering the body, and/or inside the body and accounting for its trajectory and/or entry point. This may allow for reducing x-ray doses, as shots are not needed to visualize the instrument and it is instead visualized through the optical system.

As another example for a possible use for this technology, in some embodiments and implementations, a primary axis of the tool/implant may be extrapolated into an x-ray volume and may define the targeted direction with respect to anatomical organs and previously embedded, if any, surgical hardware. As another example, if the destination point has been already selected (e.g., the target 1967 from system 1900), the practitioner/user can be provided with an estimation of the distance between the actual position of the tip and the planned position of the tip, measured along the tool axis.

In some embodiments and implementations, one or more images collected from a tracking system, such as a 3D optical image reconstruction system, may be used in a smart user interface to disambiguate the actual tool/implant of interest vs. any other instrumentation/objects that may be in the image. For example, by identifying the tool/implant that is in a surgeon's hand, a mass attenuation volumetric reconstruction can be more accurately re-sliced based on analysis of the mass attenuation reconstruction. For example, single value decomposition can be used to identify a long tool axis or another suitable axis of a movable object relative to the region of interest.

Knowledge of the instrument/tool/implant position and its extended trajectory from a tracking system may also be used to define a local region of interest for a mass attenuation reconstruction system. This may allow the system to reconstruct a volume that can be centered around the instrument and therefore can be smaller, have higher resolution, and/or exclude extraneous objects. This may reduce the reconstruction time and may improve the reconstruction resolution. Another benefit of some implementations of this method is that it may make the reconstruction more robust by excluding other objects. This may be especially true when reconstructing a specific data layer, such as the instrument or implant layer in a reconstruction algorithm. The local region of interest can also be of a different dimension. For example, a 2D slice that is linked to the instrument/tool/implant geometry may be taken, which may further speed up reconstruction as a 2D reconstruction is orders of magnitude faster than 3D reconstruction.

As another example of an instrument/tool reconstruction improvement, data from a tracking system may be used to constrain the reconstruction of a 3D x-ray image system by providing additional information about the reconstructed object, such as geometric information (diameter, length, etc.), material composition (for example by associating colors and reflection or opacity to, for example, different instrument/implant densities), and/or other information. Such information can be used to constrain the instrument/implant reconstruction from the x-ray system. Indeed, preliminary data generated by the applicant shows that a density constraint may strongly improve reconstruction. The automatic visual identification of an instrument/implant may be done by identifying certain attributes (for example, a color and/or sizes given a surgical toolkit from a given manufacturer) into a limited space of possibilities, such as the possible values within a specific surgical tool set being used. This may add an additional dimension of information on the correct width, length, or other parameters of the instrument/implant in the case of geometric information. Alternatively, or additionally, this may allow the reconstruction to use a specific density reconstruction constraint for the instrument/implant reconstruction layer, thereby improving image quality. These constraints can be statistical constraints as well as hard constraints.

In another example of a combined 3D x-ray image reconstruction system and 3D optical image reconstruction system, the combined system may allow both the 3D tracking system and a mass attenuation 3D reconstruction system to reconstruct with a common framework (or reducible to a common framework) that may be, a priori, known based on a joint calibration step. This common framework can be used to do all of the above (e.g., aid the reconstruction, account for motion, and/or guide the surgery, etc.) in a simple way without requiring a separate registration step, which could otherwise be intraoperative or real time, which in the surgical case, for example, may impair the surgical workflow. The joint calibration step may, in some implementations, be most accurately achieved by using a common x-ray geometry calibration fixture (for example, a helix x-ray calibration phantom, or the "cone" calibration phantom used by some tomosynthesis systems), where the same markers may be visible in both the x-ray system and the optical system (for example, bbs on a plexiglass structure). Alternatively, the fixture could have separate markers at fixed and known relative positions in the fixture.

Figure 22:
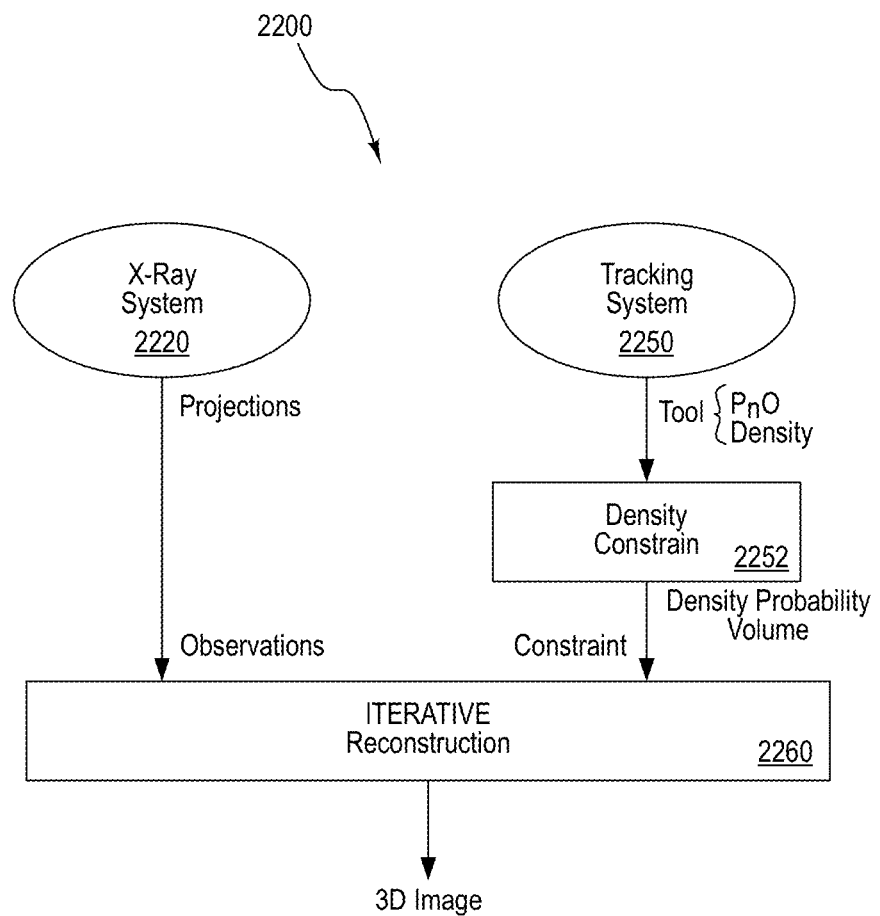
FIG. 22 is a schematic diagram illustrating the operation of an imaging system comprising a tracking system and an x-ray system according to other embodiments and implementations.

Yet another more specific example of a combined x-ray imaging and tracking system is shown in FIG. 22 at 2200. System 2200 comprises x-ray system 2220, which may comprise an x-ray tomosynthesis image reconstruction system, and tracking system 2250, which may comprise a 3D tracking system. As previously mentioned, this combined x-ray and tracking system 2200 may be used to combine data from systems 2220 and 2250 to perform a more accurate 3D reconstruction of at least a portion of an object. For example, in some embodiments and implementations, system 2200 may use tracking system 2250 to generate a density constraint, as indicated at 2252, based on a specific tracked tool or implant and/or the position of the tool/implant, that is registered to the image space.

In some embodiments and implementations, the constraint may be applied as a modification of an intermediary solution in an iterative reconstruction algorithm scheme. For example, the densities where the tool is supposed to be may be biased towards an a-priori known tool density or, as another example, the densities may be forced towards a lower density (in the human tissue range vs. stainless steel if the tool is stainless steel, for example) if there is no tool being used.

In some embodiments and implementations, tracking system 2250 may provide tool/implant identification (and therefore an a-priori of the tool/implant density) and the tool/implant PnO may be registered to the x-ray imaging system 2220. The tool/implant identification and the PnO may then be used to build a density constraint at 2252 (for example, a transfer function that forces densities closer to the tool in the areas where the tool is and/or forces lower densities in areas where there is no tool). The x-ray system 2220 may also provide projections of at least two imaged objects (for example, a surgical tool and a portion of patient anatomy).

An iterative reconstruction may be performed at 2260 to generate a 3D image. In some embodiments and implementations, an algorithm with a constraint term such as an iterative reconstruction algorithm with regularization, penalization or other constraint, that uses an identified constraint and/or projections may be used to provide an image of the combined objects.

It will be understood by those having skill in the art that changes may be made to the details of the above-described embodiments without departing from the underlying principles presented herein. For example, any suitable combination of various embodiments, or the features thereof, is contemplated.

In any methods disclosed herein comprising one or more steps or actions for performing the described method, the method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment.

Those having skill in the art will appreciate that many changes may be made to the details of the above-described embodiments without departing from the underlying principles of the invention. The scope of the present invention should, therefore, be determined only by the following claims.

The invention claimed is:

1. An imaging system, comprising:
an x-ray tomosynthesis image reconstruction system configured to generate three-dimensional image data of a region of interest of a target object under a surface of the target object;
a three-dimensional optical imaging system configured to generate surface three-dimensional image data of at least a portion of the target object, wherein the optical imaging system is registered to the x-ray tomosynthesis image reconstruction system, wherein the three-dimensional optical imaging system is further configured to generate surface three-dimensional image data of a tool to be inserted into the region of interest of the target object wherein the tool comprises a surgical instrument, and wherein the three-dimensional optical imaging system is further configured to generate surface three-dimensional image data of the tool as the tool moves relative to the surface of the target object;
a processor configured to compile the surface three-dimensional image data of the tool over time and derive a trajectory of the tool relative to the target object, wherein the system is configured to allow a user to select a preferred trajectory for the surgical instrument relative to the region of interest, and wherein the processor is configured to dynamically calculate a variance metric between the preferred trajectory and the trajectory; and
a display configured to display at least a portion of the region of interest and to dynamically display a trajectory of the tool relative to the region of interest.

2. The imaging system of claim 1, wherein the display is configured to display at least one of a number corresponding with the variance metric and an image illustrating both the trajectory and the preferred trajectory.

3. The imaging system of claim 1, wherein the system is configured to allow a user to select a target within the region of interest of the target object, and wherein the system is configured to dynamically display a distance between the tool and the target.

4. The imaging system of claim 1, wherein the imaging system is configured to dynamically adjust the region of interest in response to movement of the tool.

5. The imaging system of claim 4, wherein the imaging system is configured to dynamically define the region of interest so as to contain a point adjacent to a distal tip of the tool.

6. The imaging system of claim 5, wherein the imaging system is configured to dynamically modify the display as the region of interest is defined by movement of the distal tip of the tool.

7. An imaging system, comprising:
an x-ray tomosynthesis image reconstruction system configured to generate three-dimensional image data of a region of interest of a target object under a surface of the target object;
a three-dimensional optical imaging system configured to generate surface three-dimensional image data of at least a portion of the target object, wherein the optical imaging system is registered to the x-ray tomosynthesis image reconstruction system, wherein the three-dimensional optical imaging system is further configured to generate surface three-dimensional image data of a tool to be inserted into the region of interest of the target object, and wherein the three-dimensional optical imaging system is further configured to generate surface three-dimensional image data of the tool as the tool moves relative to the surface of the target object;
a processor configured to compile the surface three-dimensional image data of the tool over time and derive a trajectory of the tool relative to the target object; and
a display configured to display at least a portion of the region of interest and to dynamically display a trajectory of the tool relative to the region of interest,
wherein the imaging system is configured to dynamically adjust the region of interest in response to movement of the tool, wherein the imaging system is configured to dynamically define the region of interest so as to contain a point adjacent to a distal tip of the tool.

8. The imaging system of claim 7, wherein the tool comprises a surgical instrument.

9. The imaging system of claim 8, wherein the system is configured to allow a user to select a preferred trajectory for the surgical instrument relative to the region of interest, and wherein the processor is configured to dynamically calculate a variance metric between the preferred trajectory and the trajectory.

10. The imaging system of claim 9, wherein the display is configured to display at least one of a number corresponding with the variance metric and an image illustrating both the trajectory and the preferred trajectory.

11. The imaging system of claim 7, wherein the system is configured to allow a user to select a target within the region of interest of the target object, and wherein the system is configured to dynamically display a distance between the tool and the target.

12. The imaging system of claim 7, wherein the imaging system is configured to dynamically modify the display as the region of interest is defined by movement of the distal tip of the tool.

* * * * *